(12) United States Patent
Ying et al.

(10) Patent No.: US 11,873,508 B2
(45) Date of Patent: Jan. 16, 2024

(54) THERMORESPONSIVE MICROCARRIER SYSTEM AND USES THEREOF

(71) Applicant: AGENCY FOR SCIENCE, TECHNOLOGY AND RESEARCH, Singapore (SG)

(72) Inventors: Jackie Y. Ying, Singapore (SG); Leng Leng Chng, Singapore (SG); Daniele Zink, Singapore (SG); Aysha Farwin, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 575 days.

(21) Appl. No.: 16/473,266

(22) PCT Filed: Jan. 22, 2018

(86) PCT No.: PCT/SG2018/050040
§ 371 (c)(1),
(2) Date: Jun. 25, 2019

(87) PCT Pub. No.: WO2018/136015
PCT Pub. Date: Jul. 26, 2018

(65) Prior Publication Data
US 2020/0149001 A1    May 14, 2020

(30) Foreign Application Priority Data
Jan. 20, 2017  (SG) ............................ 10201700482T

(51) Int. Cl.
*C12N 5/00*     (2006.01)
*C08F 293/00*   (2006.01)
*C08L 53/00*    (2006.01)
*C12N 5/0775*   (2010.01)

(52) U.S. Cl.
CPC ........ *C12N 5/0075* (2013.01); *C08F 293/005* (2013.01); *C08L 53/005* (2013.01); *C12N 5/0662* (2013.01); *C08F 2438/00* (2013.01); *C08F 2810/20* (2013.01); *C08F 2810/50* (2013.01); *C08L 2207/53* (2013.01); *C08L 2312/00* (2013.01); *C12N 2500/90* (2013.01); *C12N 2500/98* (2013.01); *C12N 2531/00* (2013.01); *C12N 2533/30* (2013.01); *C12N 2539/10* (2013.01)

(58) Field of Classification Search
None
See application file for complete search history.

(56) References Cited

U.S. PATENT DOCUMENTS 5,173,421 A   12/1992  Kiniwa et al.
8,404,485 B2   3/2013  McCarthy et al.

FOREIGN PATENT DOCUMENTS

CN    103911853 A       7/2014
JP    2006-174826 A     7/2006
WO    WO-2010/138702 A1 12/2010
WO    WO-2013/158048 A1 10/2013

OTHER PUBLICATIONS

Chuah et al., Scientific Reports, 5:18162, pp. 1-12, 2015 (Year: 2015).*
Kim et al., Macromolecular Bioscience 2016, vol. 16, pp. 738-747 (Year: 2016).*
Yang et al., Cell Transplantation, vol. 19, pp. 1123-1132, 2010 (Year: 2010).*
Lee et al., Mussel-Inspired Surface Chemistry for Multifunctional Coatings, Science Oct. 19, 2007, vol. 319,pp. 426-430 (Year: 2007).*
Search Report and Written Opinion in International Application No. PCT/SG2018/050040 dated Mar. 23, 2018, 11 pages.
Alam et al., "Micron Sized pH-Thermosensitive Composite Polymer Particles Based on 2-Dimethylaminoethyl Methacrylate and N-Isopropyl Acrylamide", Journal of Polymer Materials, vol. 21, No. 1, Mar. 31, 2005, pp. 37-43.
Si et al., "Distribution of Carboxyl Groups in Monodispersed Poly(N)-isopropylacrylamide-co-acrylic acid) Microspheres Prepared by Membrane Emulsification", The Chinese Journal of Process Engineering, vol. 11, No. 2, Apr. 30, 2011, pp. 343-348.
Wan et al., "Synthesis and Swelling Properties of a pH- and termperature-dual Responsive Hydrogel by Inverse Microemulsion Polymerization", Journal of Applied Polymer Science, vol. 132, No. 26, Mar. 13, 2015, pp. 42139:1-8.
Han et al., "Polydopamine Nanoparticles Modulating Stimuli-Responsive PNIPAM Hydrogels With Cell/Tissue Adhesiveness", ACS Appl. Mater, Interfaces vol. 8, No. 42, Oct. 14, 2016, pp. 29088-29100.
Dai et al., "Effects of Culture Substrate Made of Poly(N-isopropylacrylamide-co-acrylic acid) Microgels on Osteogenic Differentiation of Mesenchyman Stem Cells", vol. 21, No. 9, Sep. 9, 2016, 10 pages.
Extended European Search Report in EP Application No. 18741579.9 dated Jul. 13, 2020, 14 pages.

(Continued)

*Primary Examiner* — Evelyn Y Pyla
(74) *Attorney, Agent, or Firm* — MARSHALL, GERSTEIN & BORUN LLP

(57) ABSTRACT

There is provided a polymeric microsphere comprising a thermally responsive monomer crosslinked with a functional group monomer, wherein the functional group monomer comprises at least one of a carboxylic acid functional group or an amine functional group. The thermally responsive monomer is preferably N-isopropylacrylamide (NIPAM), and the microspheres preferably comprise a coating of polymerized catecholamines (e.g. DOPA). There is also provided a method of preparing the polymeric microsphere and uses of the polymeric microsphere in culturing, harvesting, or expanding stem cells or stromal cells. Preferably, the cells, e.g. hMSCs (human mesenchymal stem/stromal cells), are expanded or harvested in serum-free and xeno-free medium.

13 Claims, 16 Drawing Sheets

Specification includes a Sequence Listing.

(56) References Cited

OTHER PUBLICATIONS

Second Office Action in EP Application No. 18741579.9 dated Aug. 3, 2021, 9 pages.
Hsiue et al., "Development of in situ thermosensitive drug vehicles for glaucoma therapy", Biomaterials 24, 2003, pp. 2423-2430.
Office Action in CN Application No. 2018800068725 dated Oct. 20, 2022, 22 pages.
Si, Tian bao et al., "Distribution of Carboxyl Groups in Monodispersed Poly (N-Isopropylacylamide-co-Acrylic Acid) Microspheres Prepared by Membrane Emulsification", The Chinese Journal of Process Engineering, No. 2, vol. 11, Apr. 30, 2011, pp. 343-348.
Alam et al., "Micron Sized pH-Thermosensitive Composite Polymer Particles Based on 2-Dimethylaminoethyl Methacrylate and N-Isopropyl Acrylamide", Journal of Polymer Materials, vol. 21, Mar. 31, 2005, pp. 37-43.
Second Office Action in CN Application No. 201880006872.5 dated Apr. 7, 2013, 13 pages.

\* cited by examiner

[Fig. 1]
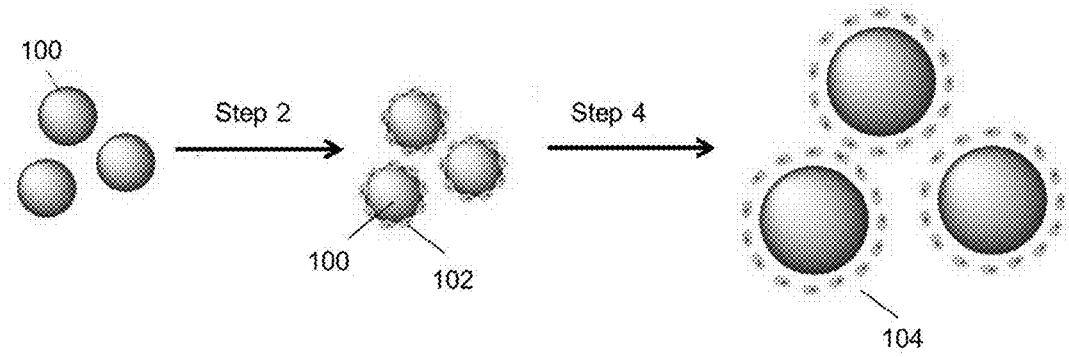

[Fig. 2]
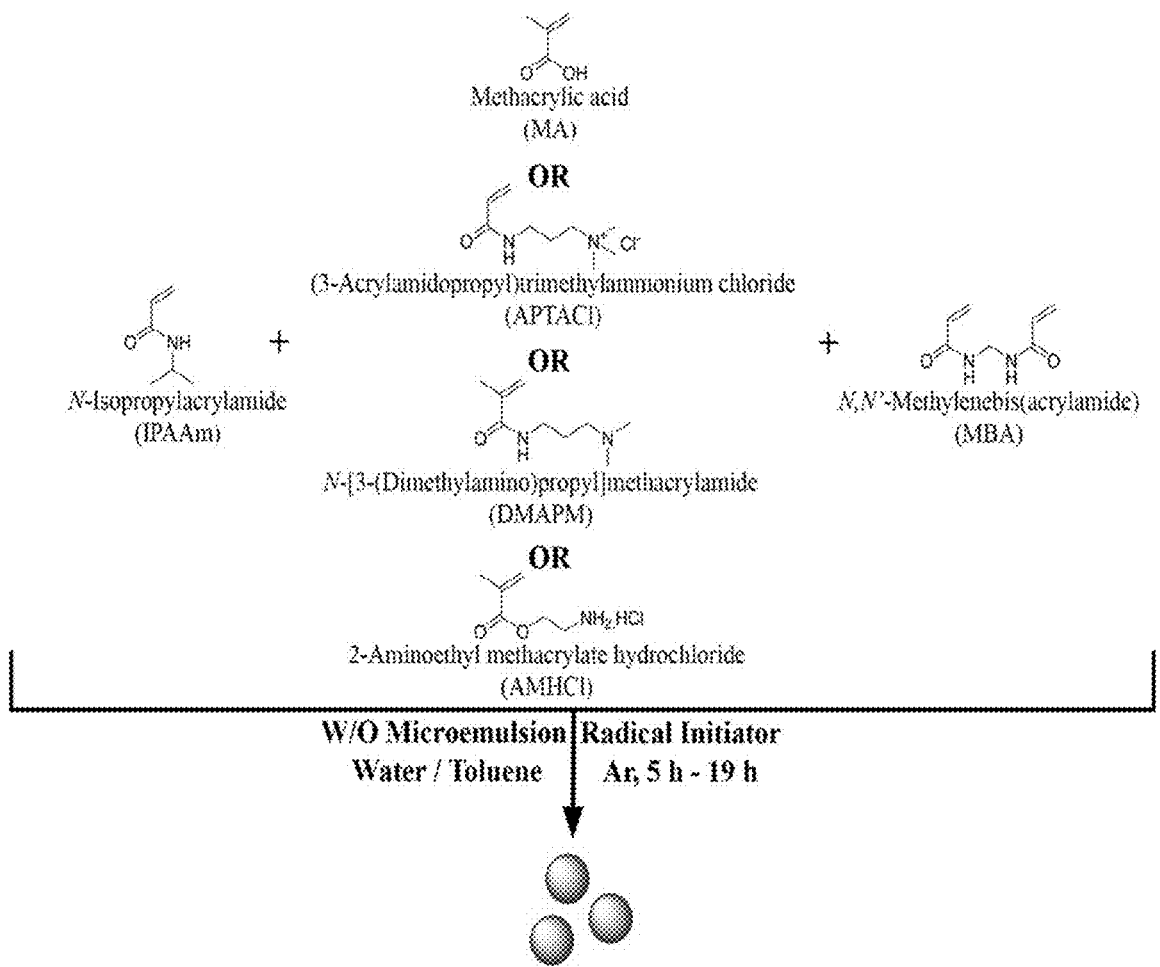

[Fig. 3]
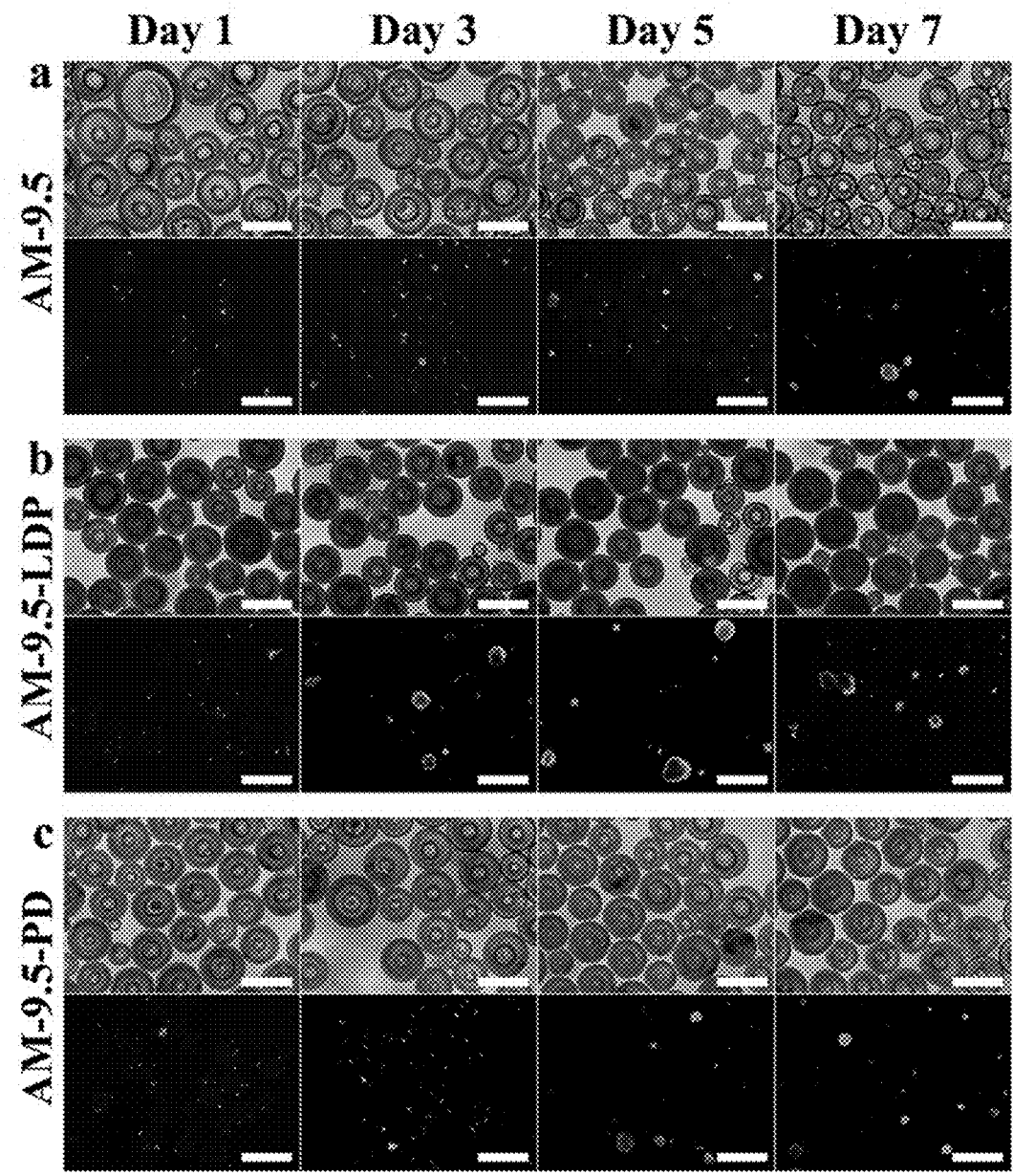

[Fig. 4]
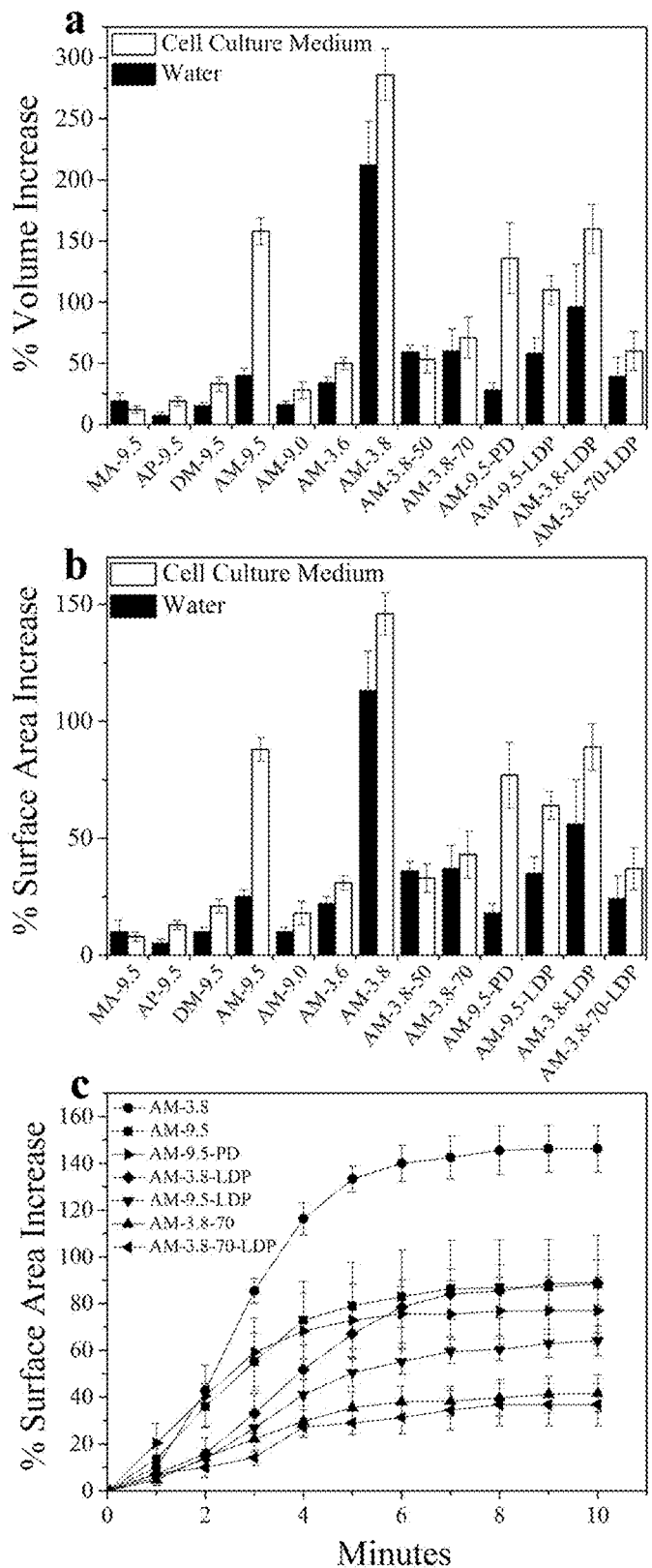

[Fig. 5]
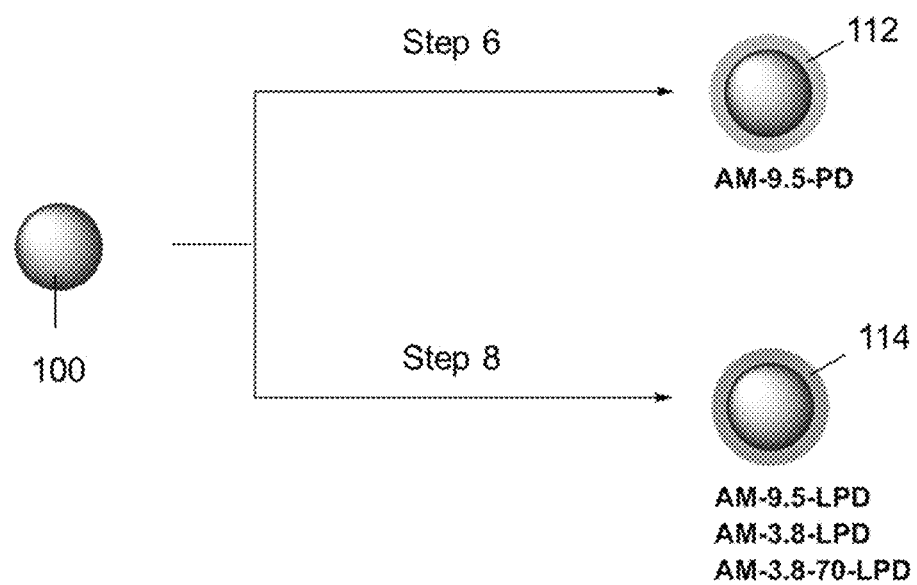

[Fig. 6]
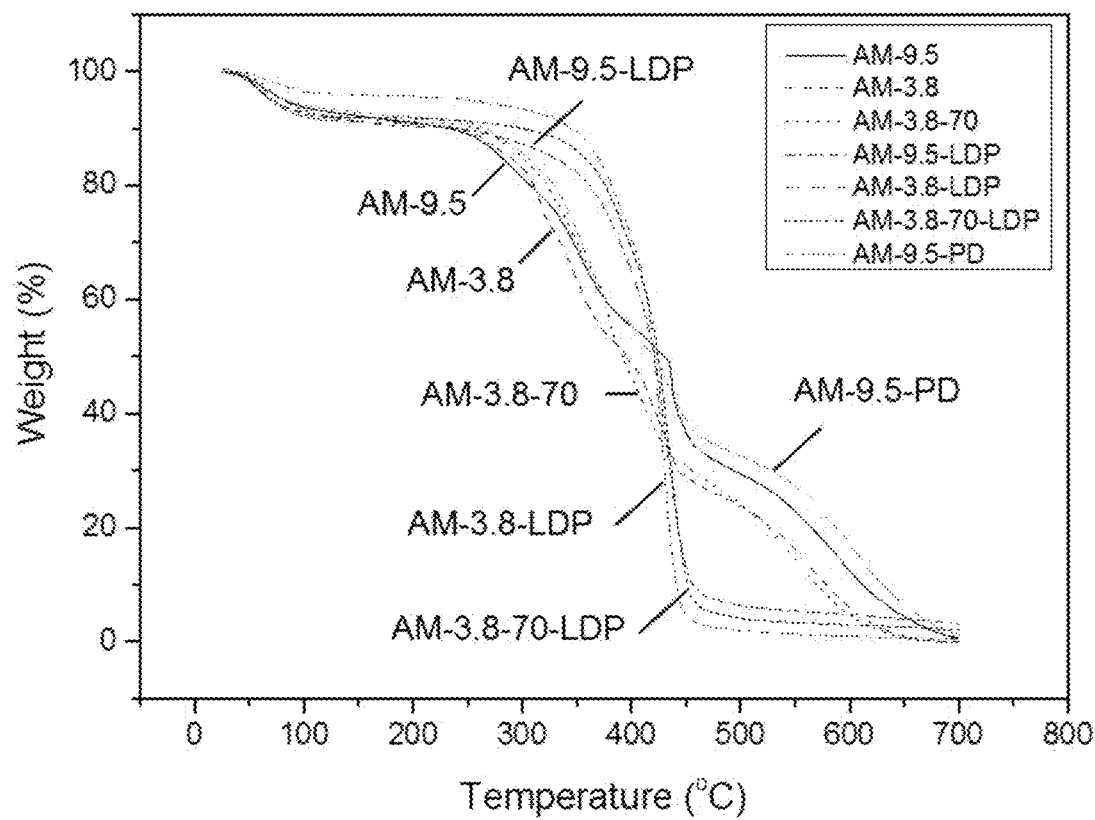

[Fig. 7]
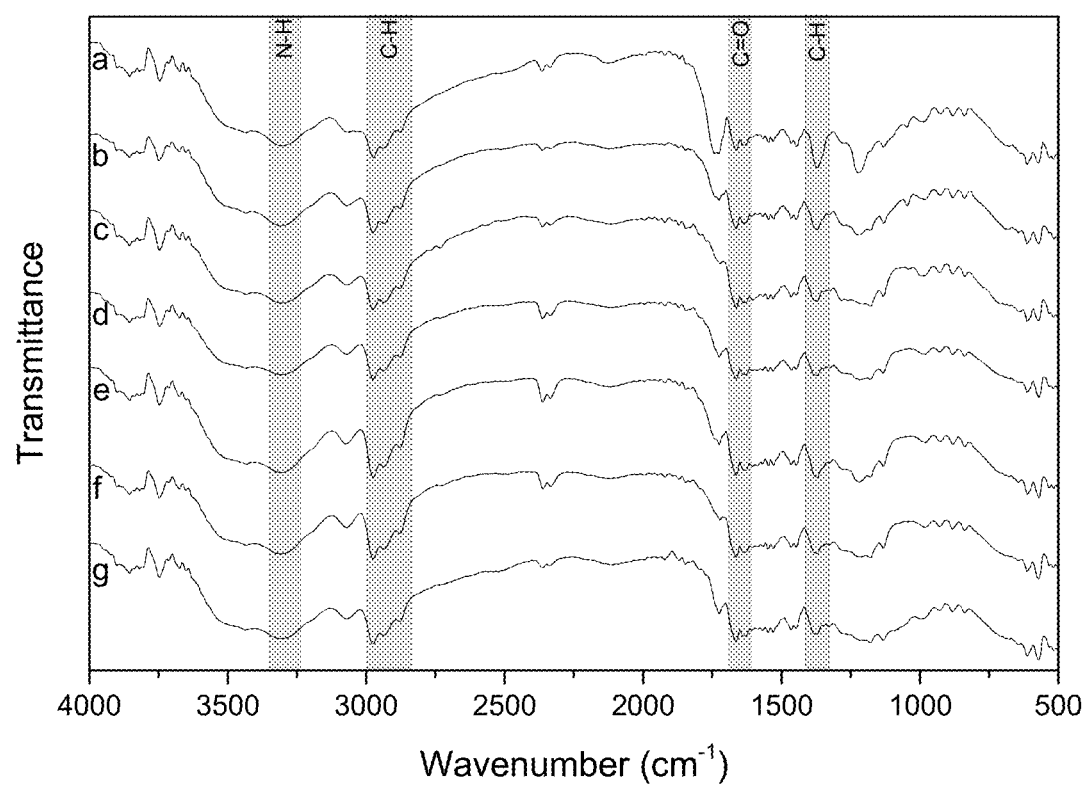

[Fig. 8]
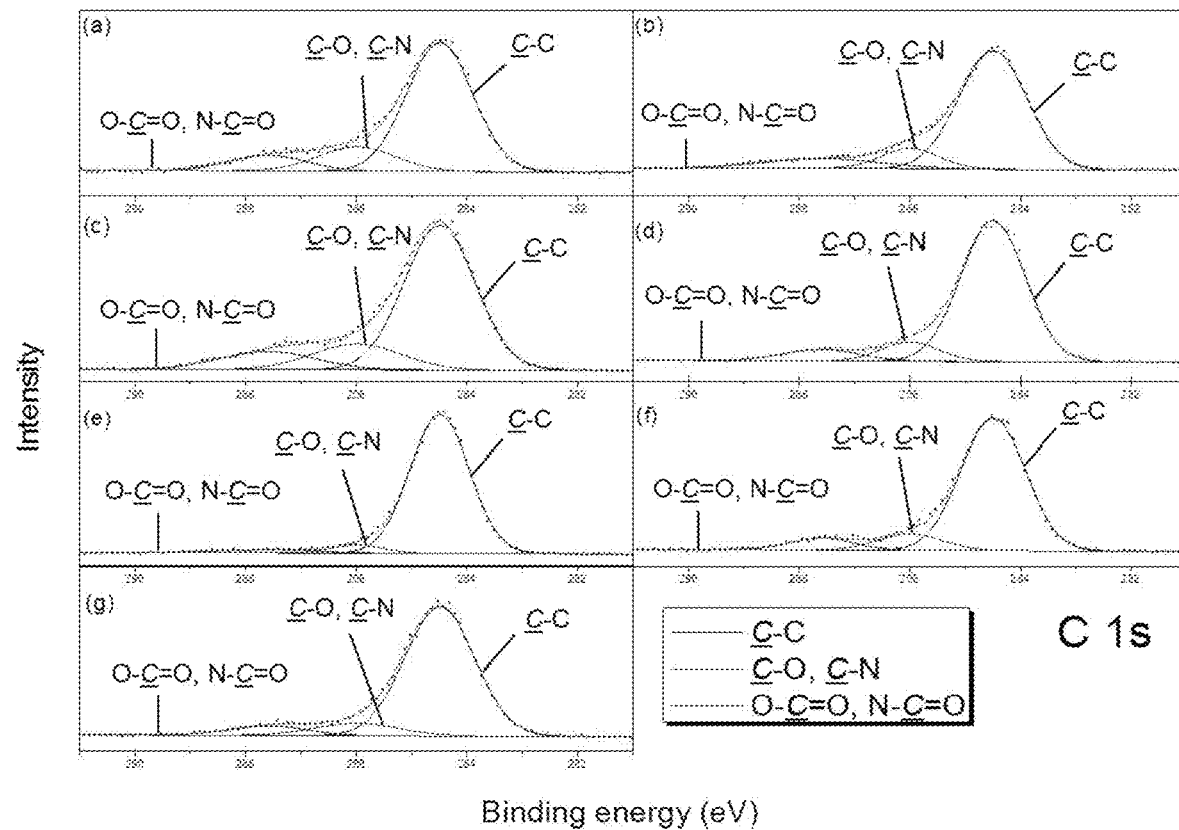

[Fig. 9]
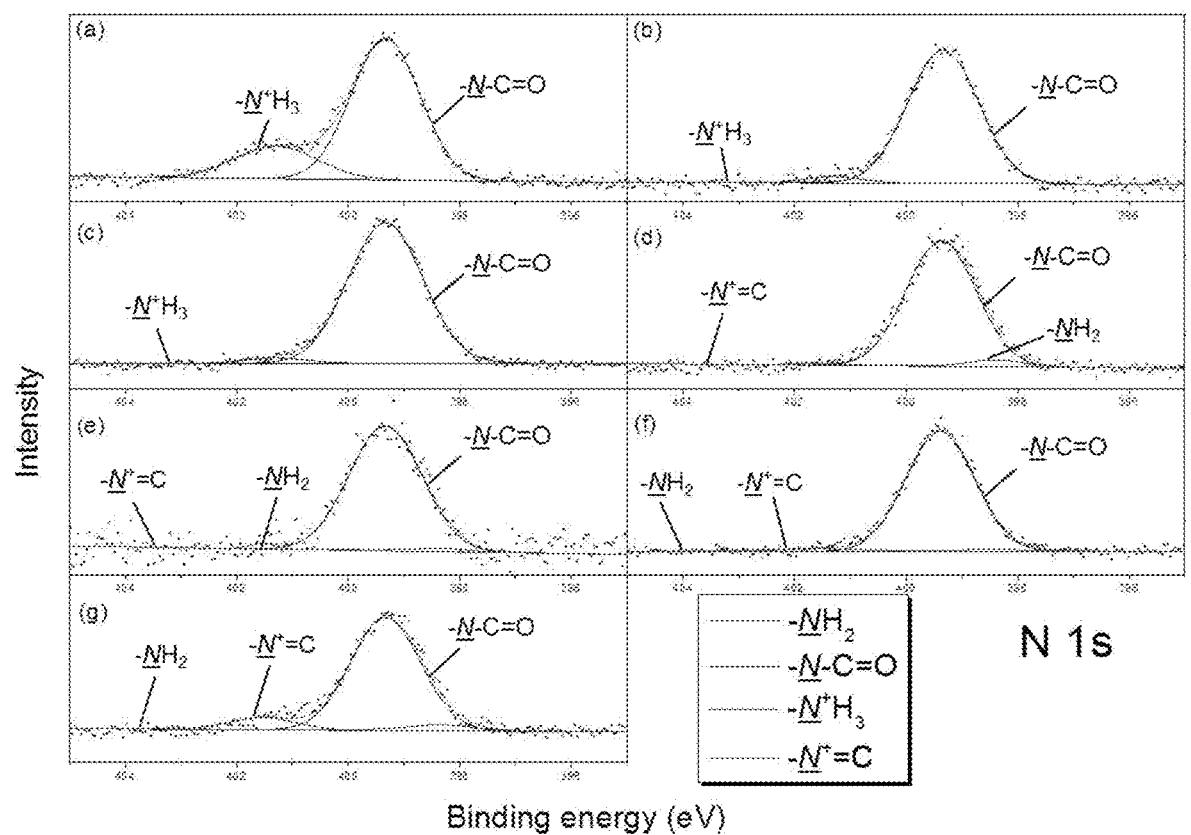

[Fig. 10]
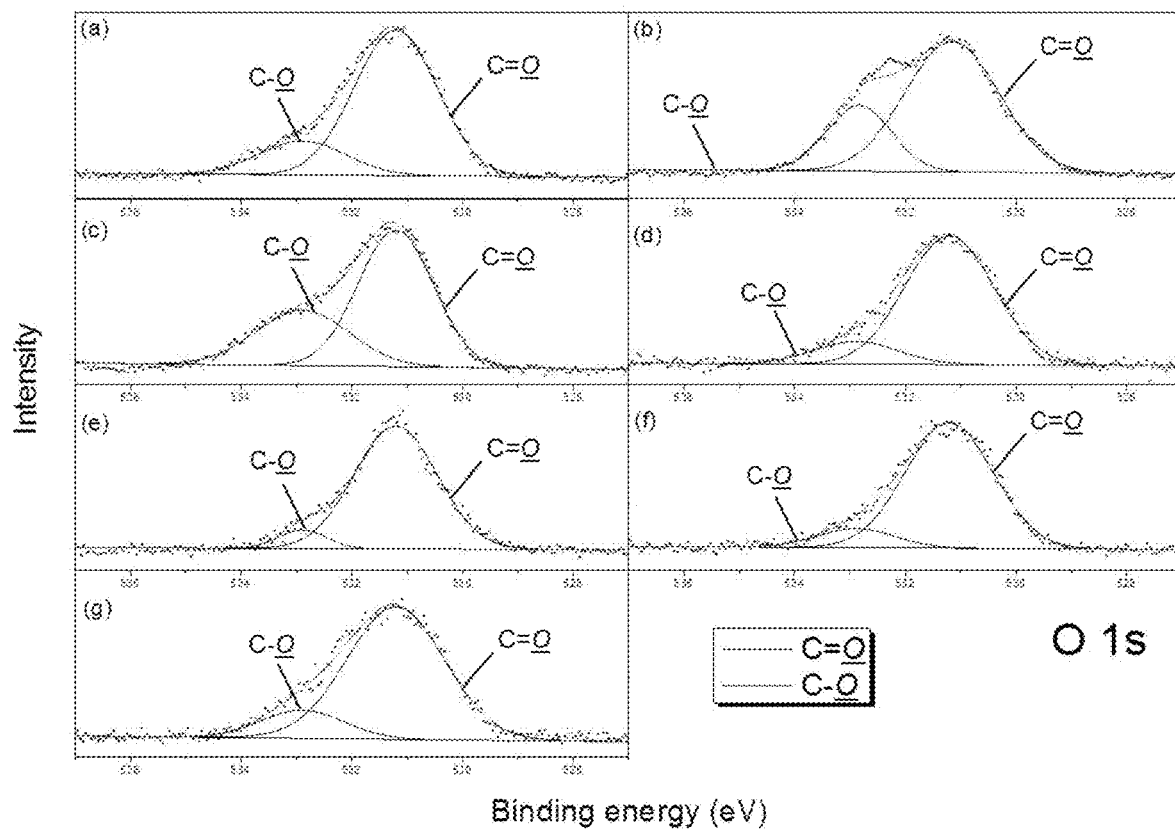

[Fig. 11]
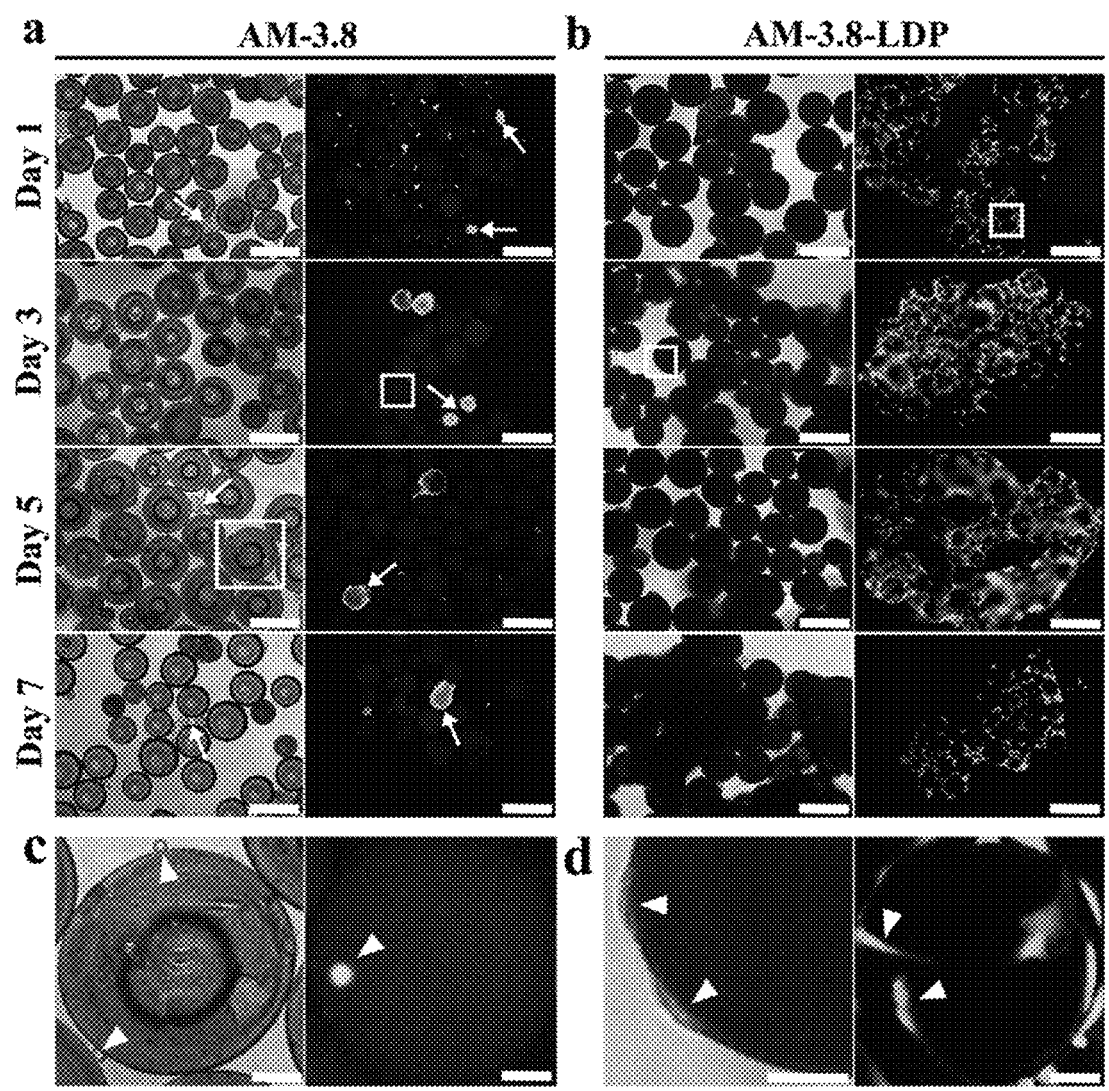

[Fig. 12]
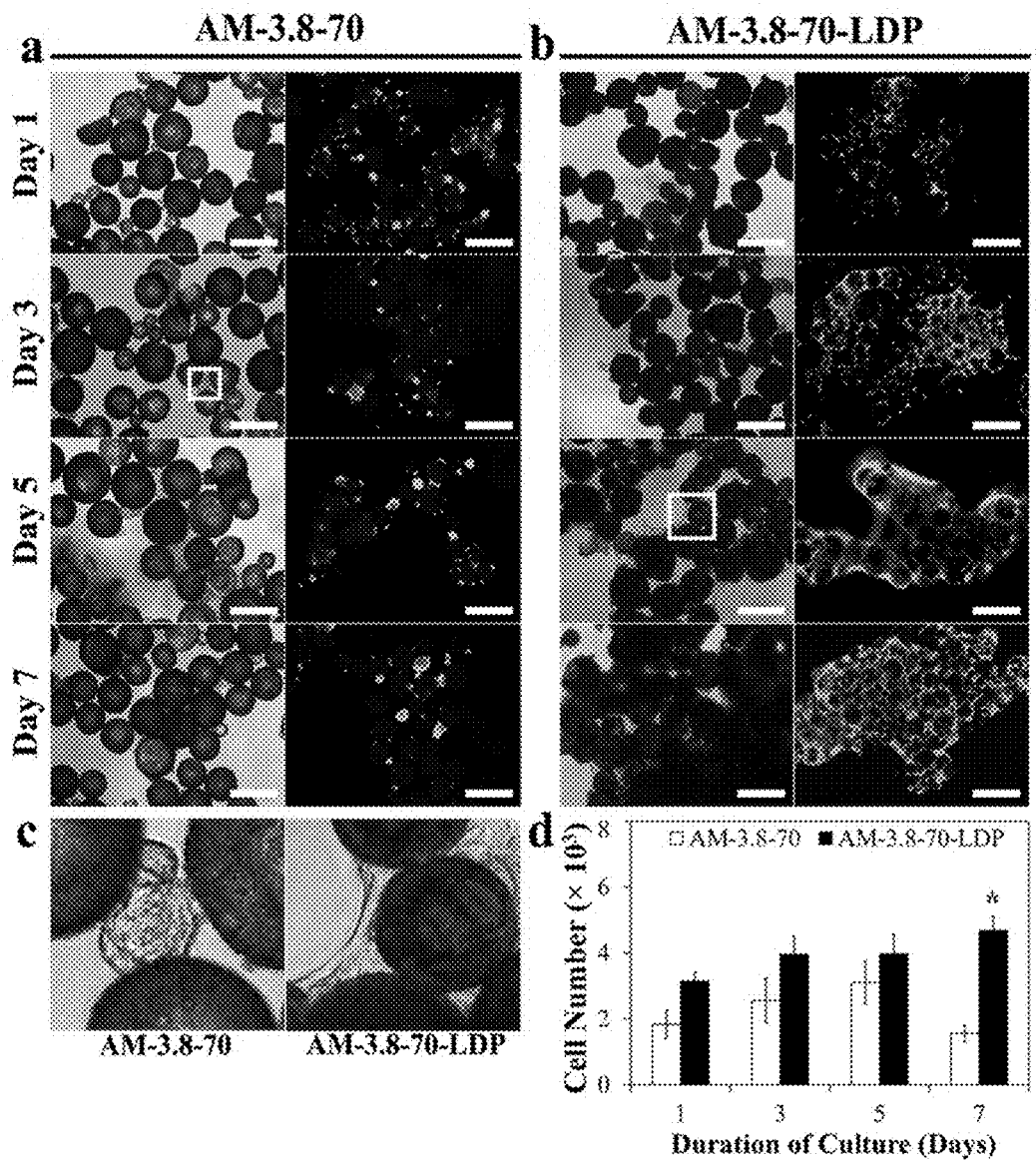

[Fig. 13]
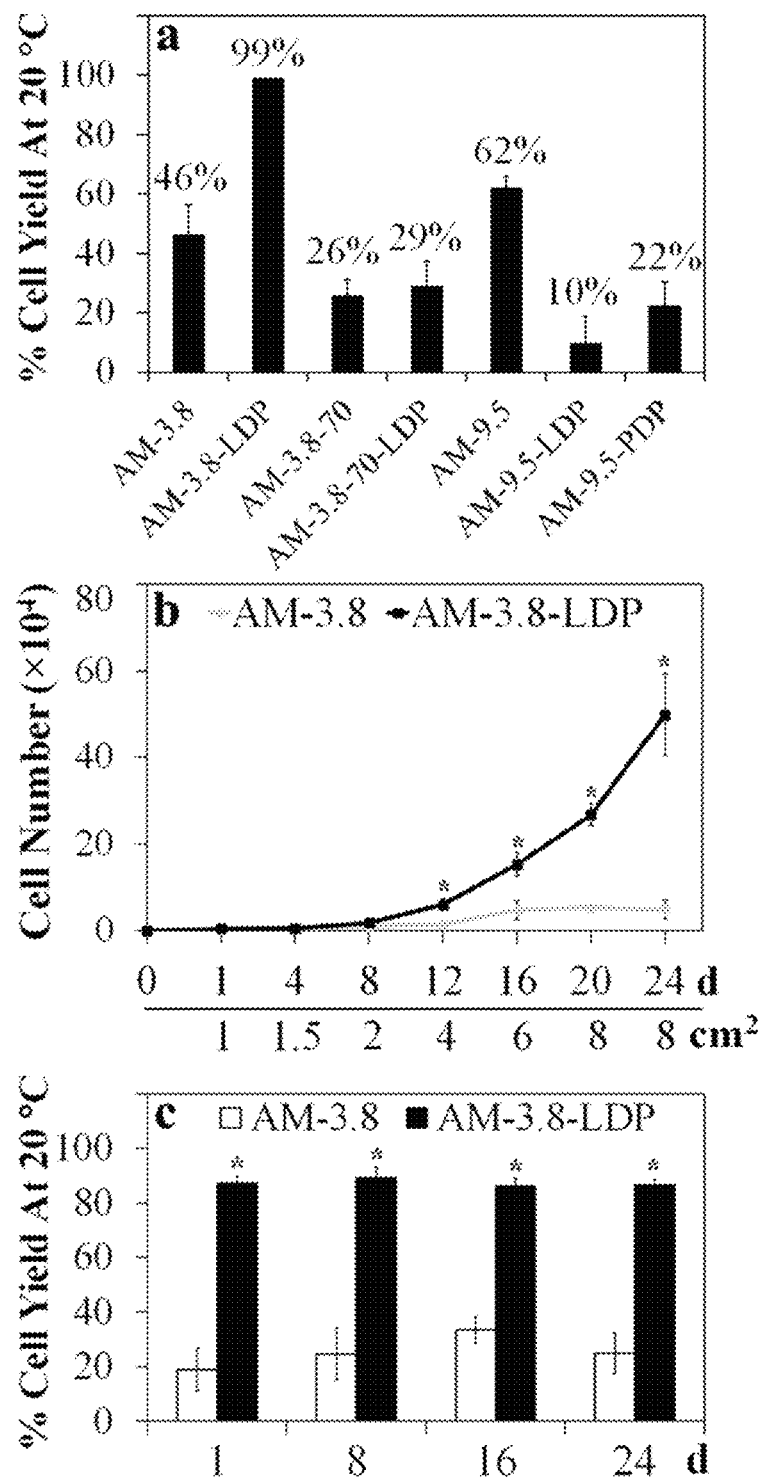

[Fig. 14]
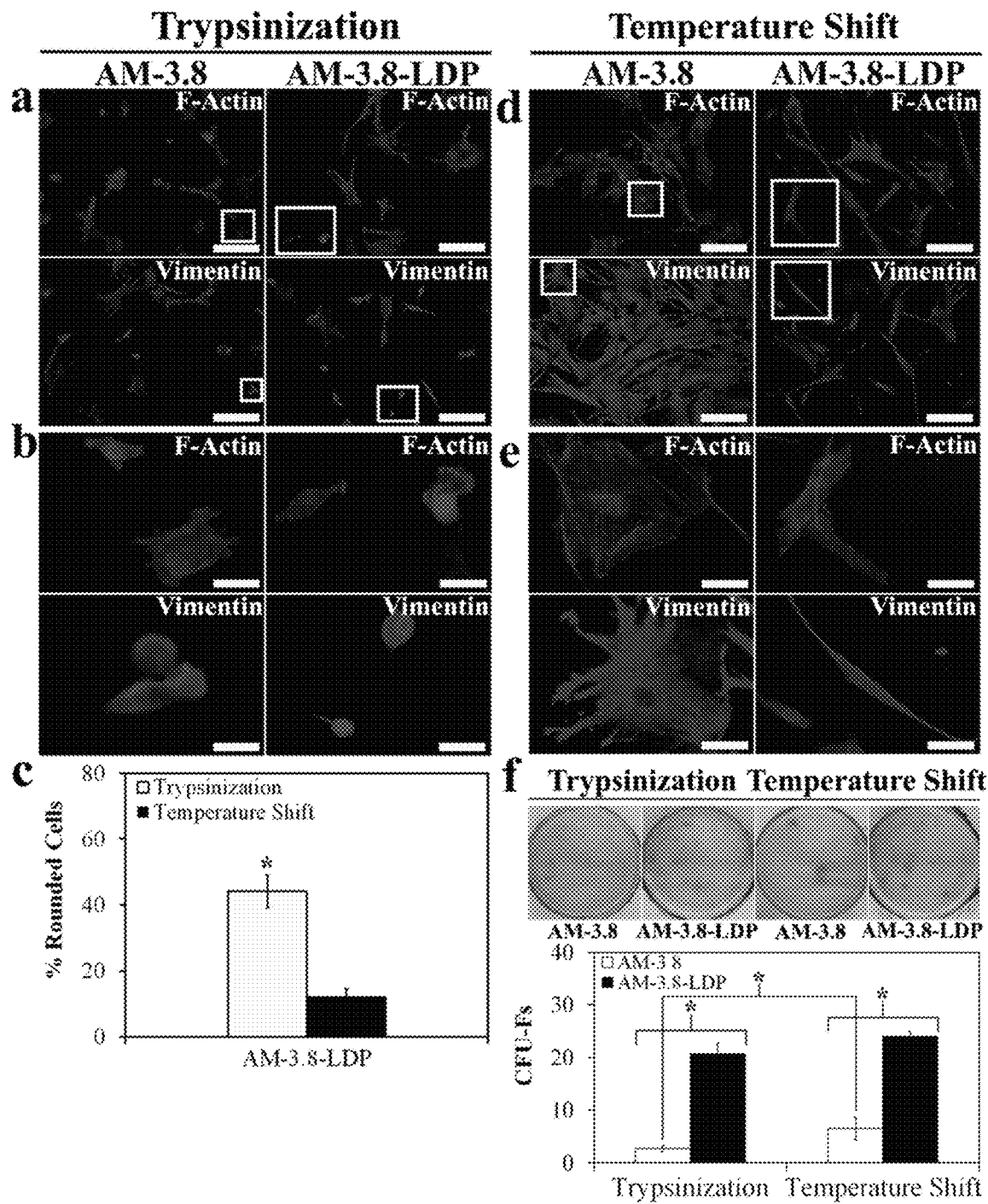

[Fig. 15]
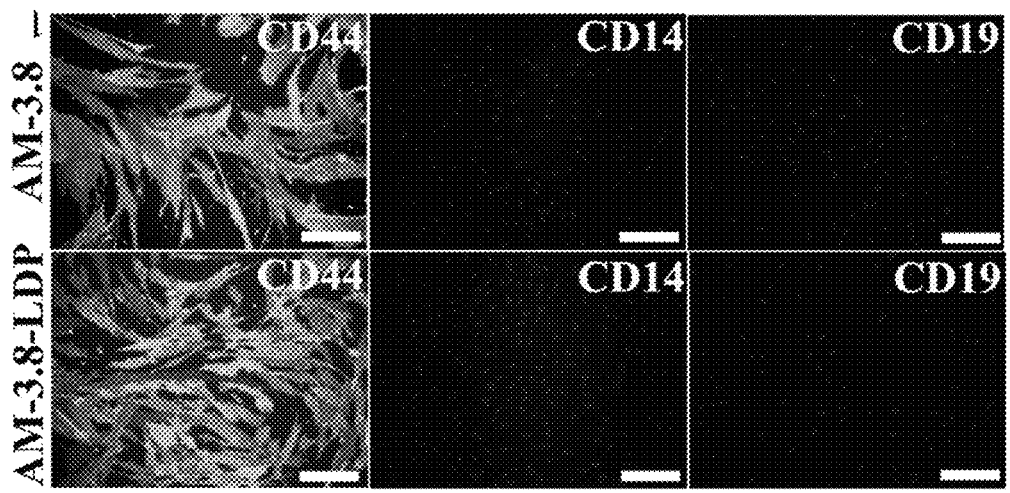

[Fig. 16]
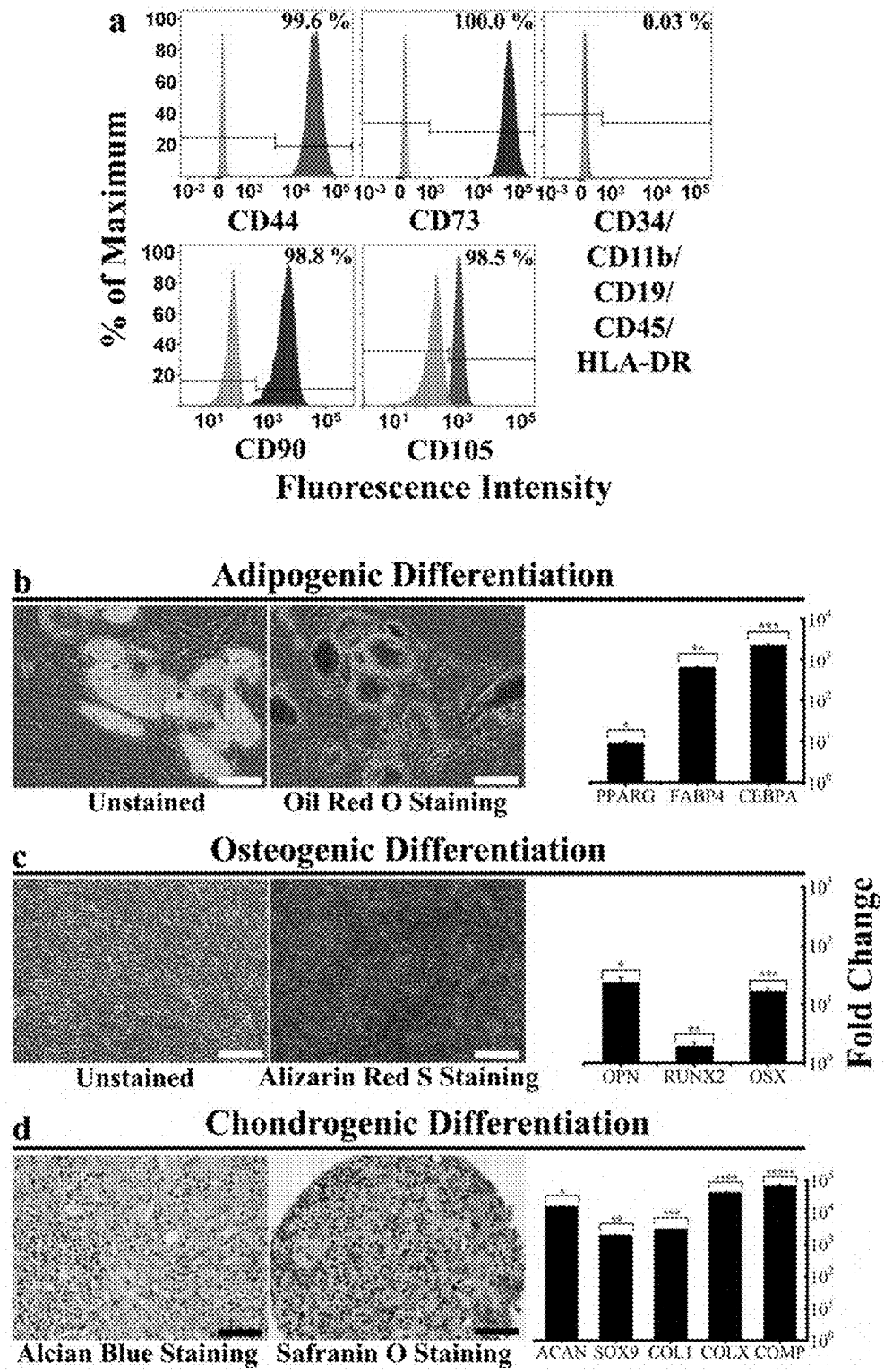

THERMORESPONSIVE MICROCARRIER SYSTEM AND USES THEREOF

TECHNICAL FIELD

The present invention generally relates to a thermoresponsive microcarrier and uses thereof. The present invention also relates to a method of preparing a thermoresponsive microcarrier.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "54253_Seqlisting.txt", which was created on Sep. 15, 2023, and is 4,828 bytes in size. The subject matter of the Sequence Listing is incorporated herein in its entirety by reference.

BACKGROUND ART

Human mesenchymal stem/stromal cells (hMSCs) have high potential for regenerative therapies. The numbers of clinical trials with human mesenchymal stem/stromal cells (hMSCs) are rapidly increasing. Clinical trials with hMSCs are performed all over the world for potential treatment of graft-versus-host disease, liver diseases, stroke, myocardial infarction, autoimmune disorders, neurodegenerative diseases, acute organ injuries, bone and cartilage diseases, and many other conditions. Clinical applications require large numbers of hMSCs that have been expanded under defined xeno-free conditions where the large hMSC doses are in the range of $10^7$ to $10^9$ cells per patient. Microcarrier-based culture systems are the most suitable system for scalable hMSC expansion and for clinical applications, and the cells should have been expanded under defined xeno-free conditions. Hence, xeno-free microcarrier systems for hMSC expansion are currently being developed.

Efficient cell harvesting by methods that do not compromise cell quality and functionality is another requirement for clinical applications. Treatment with proteolytic enzymes damages cell surface and extracellular matrix (ECM) proteins, and disrupts cell-cell interactions, resulting in irreversible cell damage, increased cell death, decreased differentiation potential and decreased grafting efficiency. Therefore, current approaches on the treatment of bone defects involved implantation of MSCs attached to microcarriers in order to avoid enzymatic harvesting. However, implantation of biodegradable microcarriers can potentially trigger inflammatory and immune reactions. While microcarrier implantation may be tolerable for some applications, such as bone regeneration, it is a problem to introduce microcarriers into severely damaged tissue, such as in the case of liver cirrhosis or acute mycocardial infarction.

An alternative to the implantation of biodegradable microcarriers is the use of non-invasive cell-harvesting techniques, such as electrically induced, pH change induced, light-induced and thermal-induced methods. The first three methods were applied only to flat surfaces, and pH changes may damage cells. The thermal-induced method has been employed for both flat surfaces and microcarrier systems.

However, current studies on cell cultivation with thermoresponsive microcarriers require the presence of serum. There are currently no thermoresponsive microcarrier systems that are able to be used in serum- and xeno-free conditions.

There is a need to provide a microcarrier system or a polymeric microsphere that overcomes, or at least ameliorates, one or more of the disadvantages described above.

SUMMARY OF INVENTION

According to one aspect, there is provided a polymeric microsphere comprising a thermally responsive monomer crosslinked with a functional group monomer, wherein the functional group monomer comprises at least one of a carboxylic acid functional group or an amine functional group.

Advantageously, the polymeric microsphere may be suitable for the scalable expansion of stems cells or stromal cells (such as human mesenchymal stem/stromal cells) under serum- and xeno-free conditions, and may allow efficient non-invasive harvesting. This may be achieved by (i) generating an entirely thermoresponsive polymeric microsphere containing a thermally responsive monomer crosslinked with a functional group monomer throughout the matrix, that is capable to change in volume and surface area when the temperature of the microsphere is lowered to a reduced temperature (such as at room temperature or 20° C.). Additionally, the entire thermoresponsive microcarrier may be coated with a polymer coating.

According to another aspect, there is provided a method of preparing a polymeric microsphere comprising a thermally responsive monomer crosslinked with a functional group monomer, wherein the functional group monomer comprises at least one of a carboxylic acid functional group or an amine functional group, wherein the method comprises the steps of:
  i. providing a microemulsion mixture of the thermally responsive monomer, the functional group monomer and the cross-linker stirring at a temperature for a period of time; and
  ii. polymerizing said microemulsion mixture with an initiator, stirring at a temperature for a period of time to thereby synthesize said microsphere.

According to another aspect, there is provided use of a polymeric microsphere for cultivating stem cells or stromal cells, wherein the polymeric microsphere comprises a thermally responsive monomer crosslinked with a functional group monomer, and wherein the functional group monomer comprises at least one of a carboxylic acid functional group or an amine functional group.

According to a further aspect, there is a method of culturing stem cells or stromal cells comprising the step of cultivating the stem cells on a surface coated on a polymeric microsphere, wherein said polymeric microsphere comprises a thermally responsive monomer crosslinked with a functional group monomer, and wherein the functional group monomer comprises at least one of a carboxylic acid functional group or an amine functional group.

According to yet another aspect, there is a method of harvesting stem cells or stromal cells comprising the step of detaching the stem cells or stromal cells from a surface coated on a polymeric microsphere, wherein said polymeric microsphere comprises a thermally responsive monomer crosslinked with a functional group monomer, and wherein the functional group monomer comprises at least one of a carboxylic acid functional group or an amine functional group. According to a further aspect, there is a method of expanding and harvesting stem cells or stromal cell comprising the steps of growing and detaching the stem cells or stromal cells from a surface coated on a polymeric microsphere, wherein said polymeric microsphere comprises a thermally responsive monomer crosslinked with a functional group monomer, and wherein the functional group monomer comprises at least one of a carboxylic acid functional group or an amine functional group.

Definitions

The following are some definitions that may be helpful in understanding the description of the present invention. These are intended as general definitions and should in no way limit the scope of the present invention to those terms alone, but are put forth for a better understanding of the following description.

The following words and terms used herein shall have the meaning indicated:

The term "serum-free condition" as used herein refers to cultivation of a cell in a condition which essentially is free of serum of any type. Non-limiting example of a serum which is not used in the present application is fetal bovine serum.

The term "xeno-free condition" as used herein refers to cultivation of a cell in a condition which does not have any human or animal component. It is possible that the term "xeno-free condition" may include trace amounts of human or animal component depending on the type of cell to be cultured but it is expected that such components, if present, would be less than 1% and were not intentionally added, and were also not regular part of any of the reagents or media components that were used.

The term "room temperature" as used herein and commonly known are temperatures between 20° C. to 25° C. or 20° C., 21° C., 22° C., 23° C., 24° C., or 25° C.

The term "initiator" as used herein refers to a compound or a source of any chemical species that reacts with a monomer (single molecule that can form chemical bonds) to form an intermediate compound capable of linking successively with a large number of other monomers into a polymeric compound. Such compounds are capable of initiating or catalyzing chemical reactions.

The term "thermally responsive" when referring to an article, refers to the ability of the article to change at least one of its physical properties when subjected to a change in temperature. This physical property can be an increase or a decrease in the volume, surface area or at least one dimension (height, length, breadth, etc) of the article when the temperature that the article is subjected to increases or decreases. The change in the physical property may be proportional to the change in the temperature (for example, as the temperature increases, the magnitude of the physical property increases, or decreases as the temperature decreases), or may be inversely proportional (for example, as the temperature increases, the magnitude of the physical property decreases, or increases as the temperature decreases). In addition to a change in physical properties, there can be a change in chemical properties. When referring to the thermoresponsive microcarriers, the surface and volume changes, and in addition, the surface hydrophilicity changes as well.

The term "fold" as used herein refers to the equation of [expanded size of the polymeric microsphere (new size)]/[original size of the polymeric microsphere].

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a polymeric microsphere will now be disclosed.

The polymeric microsphere comprises a thermally responsive monomer crosslinked with a functional group monomer, wherein the functional group monomer comprises at least one of a carboxylic acid functional group or an amine functional group.

The polymeric microsphere may also be known as a microcarrier system.

The polymeric microsphere may further comprise a polymer coating. Advantageously, the polymer coating may improve the performance of various mammalian cell types on synthetic substrates. More advantageously, the polymer coating may make the synthetic substrate compatible for the large-scale expansion of human multipotent stem cells under defined serum-free conditions.

The polymer coating of the polymeric microsphere may be selected from the group consisting of catecholamines that can be polymerized, dopamine, L-3,4-dihydroxyphenylalanine (DOPA), epinephrine and norepinephrine.

The thermally responsive monomer may be thermoresponsive to aqueous solution. The aqueous solution may preferably be cell culture medium.

The thermally responsive monomer may be selected from the group consisting of N-isopropylacrylamide, N,N-diethylacrylamide, 2-(dimethylamino)ethyl methacrylate, N,N-dimethylacrylamide, acrylamide, 2-(diethylamino)ethyl acrylate, 2-(acryloyloxyethyl) trimethylammonium chloride, vinylcaprolactam, methyl vinyl ether, hydroxyethylmethacrylate, 4-hydroxybutyl acrylate, 2-hydroxyethyl methacrylate, 3-hydroxypropyl methacrylate, 2-carboxyethyl acrylate, 2-carboxyethyl acrylate oligomers, and poly(ethylene glycol) methacrylate.

The functional group monomer may comprise at least one of a carboxylic acid functional group or an amine functional group. The carboxylic acid functional group monomer may be selected from the group consisting of methacrylic acid, acrylic acid and 2-carboxyethyl acrylate The amine functional group monomer may be selected from the group consisting of primary amine, secondary amine, tertiary amine and quaternary ammonium. The primary amine functional group may be selected from the group consisting of 2-aminoethyl methacrylate hydrochloride, 3-aminopropyl methacrylate hydrochloride and N-(3-aminopropyl)methacrylamide hydrochloride. The secondary amine functional group may be selected from a group consisting of (2-boc-amino)ethyl methacrylate and 2-(tert-butylamino)ethyl methacrylate. The tertiary amine functional group may be selected from a group consisting of N-[3-(dimethylamino)propyl]methacrylamide, 2-(dimethylamino)ethyl methacrylate, 2-(diethylamino)ethyl acrylate, 3-(dimethylamino)propyl acrylate, 2-(diethylamino)ethyl methacrylate, 2-(diisopropylamino)ethyl methacrylate and 2-(dimethylamino)ethyl acrylate. The quaternary ammonium functional group may be selected from a group consisting of (3-acrylamidopropyl)trimethylammonium chloride, [3-(methacryloylamino)propyl]-trimethylammonium chloride, [2-(acryloyloxy)ethyl]trimethylammonium chloride and [2-(methacryloyloxy)ethyl]trimethylammonium chloride.

The thermally responsive monomer may be crosslinked with the functional group monomer by a crosslinker comprising N,N'-methylenebis(acrylamide).

The particle size of the polymeric microsphere may be in the range of about 100 to about 200 μm, about 100 to about 190 μm, about 100 to about 180 μm, about 100 to about 120 μm, about 120 to about 175 μm, about 120 to about 170 μm, about 120 to about 165 μm, about 120 to about 160 μm, about 120 to about 155 μm, about 120 to about 150 μm, about 120 to about 145 μm, about 120 to about 140 μm, about 120 to about 135 μm, about 120 to about 130 μm, about 120 to about 125 μm, about 125 to about 180 μm, about 130 to about 180 μm, about 135 to about 180 μm, about 140 to about 180 μm, about 145 to about 180 μm, about 150 to about 180 μm, about 155 to about 180 μm, about 160 to about 180 μm, about 165 to about 180 μm, about 170 to about 180 μm, about 175 to about 180 μm, about 180 to about 200 μm, or about 125 to about 177 μm.

The polymeric microsphere may have a response that arises from the use of the thermally responsive monomer. The microsphere may have been generated by crosslinking the thermally responsive monomer with a functional group monomer, wherein the functional group monomer comprises at least one of a carboxylic acid functional group or an amine functional group. In addition, the polymeric microsphere may have a polymer coating.

The polymeric microsphere may have a thermal response when the temperature is reduced. The polymeric microsphere may show a large thermal response when the temperature is reduced. The polymeric microsphere may show a small thermal response when the temperature is reduced. The polymeric microsphere may show a thermal response by increasing in volume and surface area. The particle size of the polymeric microsphere may increase when the polymeric microsphere is subjected to a reduced temperature. The particle size of the polymeric microsphere may increase due to an increase in volume and surface area when the polymeric microsphere is subjected to reduced temperature. The particle size of the polymeric microsphere may increase in the range of more than 1-fold to about 300-fold, about 10-fold to about 300-fold, about 50-fold to about 300-fold, about 100-fold to about 300-fold, about 150-fold to about 300-fold, about 200-fold to about 300-fold, about 250-fold to about 300-fold, more than 1-fold to about 10-fold, more than 1-fold to about 50-fold, more than 1-fold to about 100-fold, more than 1-fold to about 150-fold, more than 1-fold to about 200-fold or more than 1-fold to about 250-fold of the original size of the polymeric microsphere when the polymeric microsphere is subjected to reduced temperature. The original size of the polymeric microsphere may be the size of the polymeric microsphere before microsphere is exposed to a change in temperature. The temperature of the thermal response may be reduced from about 37° C. to about room temperature. The thermal response between 37° C. and room temperature may be determined in both water and cell culture medium. The thermal response of the polymeric microsphere may be in both water and cell culture medium.

The polymeric microsphere may have a hydrophilic surface when the polymeric microsphere is subjected to a reduced temperature. When the polymeric microsphere is subjected to a reduced temperature, the polymeric microsphere may have an increase in volume and surface area, and the hydrophilicity of the surface may also change. The hydrophilicity of the surface may be associated with the increased absorption of water. The hydrophilicity of the surface may or may not increase due to the increased absorption of water.

Advantageously, the thermoresponsive polymeric microsphere defined herein may experience changes in both the physical and chemical properties of the microsphere, such as changes in the volume and surface area (being physical properties) and acquiring a hydrophilic surface (being a chemical property) when the microsphere is exposed to a change in temperature. This is in comparison to conventional microcarriers that only have a thermoresponsive coating (that is, not one where the entire microcarrier is thermoresponsive) where there are no changes in the volume and surface area. More advantageously, the thermoresponsive polymeric microsphere may be changed entirely when the cells are detaching from the thermoresponsive polymeric microsphere, especially in the volume and surface area as well as acquiring the hydrophilic surface, whereas for flat microcarriers or microcarriers with a thermoresponsive coating, only the hydrophilic surface changes when the cells are detaching from those microspheres. When the cell detachment is occurring, the entire thermoresponsive microsphere with the polymer coating will have changes in the physical properties as defined above and the chemical property may remain the same.

The polymeric microsphere with the primary amine functional group monomer may show a larger volume and surface area increase especially when suspended in cell culture medium. The polymeric microsphere with the primary amine functional group monomer may have a smaller volume and surface area increase when suspended in water. When the primary amine functional group monomer is used in the polymeric microsphere, the primary amine functional group may remain positively charged in pH neutral water, and thereby retain more water molecules at 37° C.

The polymeric microsphere with tertiary amine functional group monomers may exhibit smaller thermal responses in both water and cell culture media, where the increase in volume and surface area is small, as their ionized functional groups attracted more water at 37° C. The polymeric microsphere with quaternary ammonium functional group monomers may exhibit smaller thermal responses in both water and cell culture media, where the increase in volume and surface area is small, as their ionized functional groups attracted more water at 37° C.

The composition of the functional group monomer of the polymeric microsphere may be varied accordingly. The polymeric microsphere having a small quantity of the primary amine functional group monomer and an optimal quantity of the crosslinker may have a larger thermal response, where the increase in volume and surface is large.

The thermal response of the microcarrier system may depend on the reaction temperature at which the microsphere is synthesized. The reaction temperature may be at room temperature, at 50° C., at 70° C. or in the range of about 30° C. to about 70° C., about 30° C. to about 65° C., about 30° C. to about 60° C., about 30° C. to about 55° C., about 30° C. to about 50° C., about 30° C. to about 45° C., about 30° C. to about 40° C., about 30° C. to about 35° C., about 35° C. to about 70° C., about 40° C. to about 70° C., about 45° C. to about 70° C., about 50° C. to about 70° C., about 55° C. to about 70° C., about 60° C. to about 70° C., about 65° C. to about 70° C. or more preferably at room temperature. The thermal response of the microcarrier system may be small when the reaction temperature is higher than room temperature. The small thermal response of the microcarrier system may be due to the higher degree of crosslinking between the thermally responsive monomer and the functional group monomer.

The quantity of the functional group monomer in the feed composition for the polymeric microsphere may be in the range of about 3.0 mol % to about 10.0 mol %, about 3.0 mol % to about 9.0 mol %, about 3.0 mol % to about 8.0 mol %, about 3.0 mol % to about 7.0 mol %, about 3.0 mol % to about 6.0 mol %, about 3.0 mol % to about 5.0 mol %, about 3.0 mol % to about 4.8 mol %, about 3.0 mol % to about 4.6 mol %, about 3.0 mol % to about 4.4 mol %, about 3.0 mol % to about 4.2 mol %, about 3.0 mol % to about 4.0 mol %, about 3.0 mol % to about 3.8 mol %, about 3.0 mol % to about 3.6 mol %, about 3.0 mol % to about 3.4 mol %, about 3.0 mol % to about 3.2 mol %, about 3.2 mol % to about 10.0 mol %, about 3.4 mol % to about 10.0 mol % about 3.6 mol % to about 10.0 mol %, about 3.8 mol % to about 10.0 mol %, about 4.0 mol % to about 10.0 mol %, about 4.2 mol % to about 10.0 mol %, about 4.4 mol % to about 10.0 mol %, about 4.6 mol % to about 10.0 mol %, about 4.8 mol % to about 10.0 mol %, about 5.0 mol % to about 10.0 mol %, about 6.0 mol % to about 10.0 mol %, about 7.0 mol % to about 10.0 mol %, about 8.0 mol % to about 10.0 mol %, about 9.0 mol % to about 10.0 mol %, or more preferably 3.8 mol %.

The quantity of the crosslinker of the polymeric microsphere may be in the range of about 4.0 mol % to about 10.0 mol %, about 4.0 mol % to about 9.5 mol %, about 4.0 mol % to about 9.0 mol %, about 4.0 mol % to about 8.5 mol %, about 4.0 mol % to about 8.0 mol %, about 4.0 mol % to about 7.5 mol %, about 4.0 mol % to about 7.0 mol %, about 4.0 mol % to about 6.5 mol %, about 4.0 mol % to about 6.0 mol %, about 4.0 mol % to about 5.8 mol %, about 4.0 mol % to about 5.6 mol %, about 4.0 mol % to about 5.4 mol %, about 4.0 mol % to about 5.2 mol %, about 4.0 mol % to about 5.0 mol %, about 4.0 mol % to about 4.8 mol %, about 4.0 mol % to about 4.6 mol %, about 4.0 mol % to about 4.4 mol %, about 4.0 mol % to about 4.2 mol %, about 4.2 mol % to about 10.0 mol %, about 4.4 mol % to about 10.0 mol %, about 4.6 mol % to about 10.0 mol %, about 4.8 mol % to about 10.0 mol %, about 5.0 mol % to about 10.0 mol %, about 5.2 mol % to about 10.0 mol %, about 5.4 mol % to about 10.0 mol %, about 5.6 mol % to about 10.0 mol %, about 5.8 mol % to about 10.0 mol %, about 6.0 mol % to about 10.0 mol %, about 6.5 mol % to about 10.0 mol %, about 7.0 mol % to about 10.0 mol %, about 7.5 mol % to about 10.0 mol %, about 8.0 mol % to about 10.0 mol %, about 8.5 mol % to about 10.0 mol %, about 9.0 mol % to about 10.0 mol %, about 9.5 mol % to about 10.0 mol %, or more preferably 5.1 mol %.

Exemplary, non-limiting embodiments of a method of preparing a polymeric microsphere will now be disclosed.

The method of preparing a polymeric microsphere comprising a thermally responsive monomer crosslinked with a functional group monomer, wherein the functional group monomer comprises at least one of a carboxylic acid functional group or an amine functional group comprises the steps of:
  i. providing a microemulsion mixture of the thermally responsive monomer, the functional group monomer and the cross-linker stirring at a temperature for a period of time; and
  ii. polymerizing said microemulsion mixture with an initiator, stirring at the temperature for a period of time to thereby synthesize said microsphere.

The microemulsion mixture may comprise of an organic solvent, aqueous solution and an emulsifier. The organic solvent may be a non-polar solvent. The non-polar solvent may be selected from the group consisting of toluene, pentane, hexane, cyclohexane, benzene, 1-4-dioxane, chloroform and diethyl ether. Toluene may be preferably used as the organic solvent. The aqueous solution may be preferably water. The emulsifier may be SPAN-85.

The first reaction time (in step (i)) may vary between about 5 minutes to about 60 minutes. It may vary in a range of about 5 minutes to about 60 minutes, about 10 minutes to about 60 minutes, about 15 minutes to about 60 minutes, about 20 minutes to about 60 minutes, about 25 minutes to about 60 minutes, about 30 minutes to about 60 minutes, about 35 minutes to about 60 minutes, about 40 minutes to about 60 minutes, about 45 minutes to about 60 minutes, about 50 minutes to about 60 minutes, about 55 minutes to about 60 minutes, about 5 minutes to about 10 minutes, about 5 minutes to about 15 minutes, about 5 minutes to about 20 minutes, about 5 minutes to about 25 minutes, about 5 minutes to about 30 minutes, about 5 minutes to about 35 minutes, about 5 minutes to about 40 minutes, about 5 minutes to about 45 minutes, about 5 minutes to about 50 minutes or about 5 minutes to about 55 minutes.

The second reaction time (in step (ii)) may vary between about 1 to about 20 hours, about 1 to about 19 hours, about 1 to about 18 hours, about 1 to about 17 hours, about 1 to about 16 hours, about 1 to about 15 hours, about 1 to about 14 hours, about 1 to about 13 hours, about 1 to about 12 hours, about 1 to about 11 hours, about 1 to about 10 hours, about 1 to about 9 hours, about 1 to about 8 hours, about 1 to about 7 hours, about 1 to about 6 hours, about 1 to about 5 hours, about 1 to about 4 hours, about 1 to about 3 hours, about 1 to about 2 hours, about 2 to about 20 hours, about 3 to about 20 hours, about 4 to about 20 hours, about 5 to about 20 hours, about 6 to about 20 hours, about 7 to about 20 hours, about 8 to about 20 hours, about 9 to about 20 hours, about 10 to about 20 hours, about 11 to about 20 hours, about 12 to about 20 hours, about 13 to about 20 hours, about 14 to about 20 hours, about 15 to about 20 hours, about 16 to about 20 hours, about 17 to about 20 hours, about 18 to about 20 hours, about 19 to about 20 hours, or more preferably 5 hours.

When the reaction temperature is room temperature, the initiator may be N,N,N',N'-tetramethylethylenediamine and/or ammonium persulfate. The initiator may also be potassium persulfate. The initiator may be a radical initiator.

When the reaction temperature is 50° C. or 70° C., the initiator may be 2,2'-azobis[2-(2-imidazolin-2-yl)propane] dihydrochloride, 4,4-azobis(4-cyanovaleric acid), 2,2'-azobis[N-(2-carboxyethyl)-2-methylpropionamidine]tetrahydrate, 2,2'-azobis(2-methylpropion-amidine) dihydrochloride or 2,2'-azobis[2-(2-imidazolin-2-yl) propane]. The initiator may be a radical initiator.

The reaction temperature may be in a range of about 20° C. to about 70° C., about 20° C. to about 50° C., about 20° C. to about 25° C., about 20° C. to about 30° C., about 20° C. to about 35° C., about 20° C. to about 40° C., about 20° C. to about 45° C., about 25° C. to about 50° C., about 30° C. to about 50° C., about 35° C. to about 50° C., about 40° C. to about 50° C., about 45° C. to about 50° C., about 50° C. to about 70° C., about 50° C. to about 55° C., about 50° C. to about 60° C., about 50° C. to about 65° C. or more preferably at room temperature or 50° C. or 70° C.

The polymeric microsphere may be sieved out from a plurality of microspheres with other particle size ranges. When the polymeric microsphere with a particle size range of 125 to 177 μm is sieved out, the microsphere may be used for the microcarrier system.

Exemplary, non-limiting embodiments of the use of a polymeric microsphere for the cultivating stem cells or stromal cells will now be disclosed. The polymeric microsphere is as described above. The stem cell or stromal cell may be human mesenchymal stem/stromal cells.

When the polymeric microsphere is subjected to a reduced temperature, the polymeric microsphere may absorb water and the particle size of the polymeric microsphere may increase. When the surface of the polymeric microsphere is hydrophilic and when the polymeric microsphere is expanded due to the ingress of water, the cells may detach from the hydrophilic surface. The polymeric microsphere may be able to have a thermally-induced cell detachment at room temperature.

The polymeric microsphere may be used for the expansion of human mesenchymal stem/stromal cells where the cell numbers may increase by about 30-fold to about 140-fold, about 30-fold to about 135-fold, about 30-fold to about 130-fold, about 30-fold to about 125-fold, about 30-fold to about 120-fold, about 30-fold to about 110-fold or preferably 125-fold from day 1 onwards up to day 24.

The polymeric microsphere may be used for harvesting the human mesenchymal stem or stromal cells where the cells are imaged and counted on 10 randomly selected images. The cell number harvested by a temperature shift may be in the range of about 25 to about 40 per image, about 25 to about 39 per image, about 25 to about 38 per image, about 25 to about 37 per image, about 25 to about 36 per image, about 25 to about 35 per image, about 25 to about 34 per image, about 25 to about 33 per image, about 25 to about 32 per image, about 25 to about 31 per image, about 25 to about 30 per image, about 25 to about 29 per image, about 25 to about 28 per image, about 25 to about 27 per image, about 25 to about 26 per image, about 26 to about 40 per image, about 27 to about 40 per image, about 28 to about 40 per image, about 29 to about 40 per image, about 30 to about 40 per image, about 31 to about 40 per image, about 32 to about 40 per image, about 33 to about 40 per image, about 34 to about 40 per image, about 35 to about 40 per image, about 36 to about 40 per image, about 37 to about 40 per image, about 38 to about 40 per image, about 39 to about 40 per image or more preferably 28 ±6 per image. The temperature shift may be from about 37° C. to about room temperature which is about 20° C. The percentage of cells harvested or detached from the surface of the polymeric microsphere as defined herein, may be in the range of about 20% to about 95%, about 30% to about 95%, about 40% to about 95%, about 50% to about 95%, about 60% to about 95%, about 70% to about 95%, about 80% to about 95%, about 90% to about 95%, about 20% to about 30%, about 20% to about 40%, about 20% to about 50%, about 20% to about 60%, about 20% to about 70%, about 20% to about 80% or about 20% to about 90% from day 1, day 3, day 5, day 7, day 9, day 11, day 13, day 15, day 17, day 19 or day 21 onwards.

Exemplary, non-limiting embodiments of a method of culturing stem cells or stromal cells will now be disclosed.

The method of culturing stem cells or stromal cells may comprise of the step of cultivating the stem cells or stromal cells on a surface coated on a polymeric microsphere, wherein said polymeric microsphere comprises a thermally responsive monomer crosslinked with a functional group monomer, and wherein the functional group monomer comprises at least one of a carboxylic acid functional group or an amine functional group.

The method of culturing stem cells or stromal cells may be undertaken in a serum-free condition. The method of culturing stem cells or stromal cells may be undertaken in a xeno-free condition.

Exemplary, non-limiting embodiments of a method of harvesting stem cells or stromal cells will now be disclosed.

The method of harvesting stem cells or stromal cells may comprise of the step of detaching the stem cells or stromal cells from a surface coated on a polymeric microsphere, wherein said polymeric microsphere comprises a thermally responsive monomer crosslinked with a functional group monomer, and wherein the functional group monomer comprises at least one of a carboxylic acid functional group or an amine functional group.

Exemplary, non-limiting embodiments of a method of expanding and harvesting stem cells or stromal cells will now be disclosed The method of expanding and harvesting stem cells or stromal cell may comprise of the steps of growing and detaching the stem cells or stromal cells from a surface coated on a polymeric microsphere, wherein said polymeric microsphere comprises a thermally responsive monomer crosslinked with a functional group monomer, and wherein the functional group monomer comprises at least one of a carboxylic acid functional group or an amine functional group.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 shows a schematic illustration of a thermoresponsive microsphere (100) for cell expansion (102) and subsequent thermally induced detachment (104).

FIG. 2 shows a synthesis of the thermoresponsive microcarriers.

FIG. 3 shows a number of images of hMSC performance in (a) AM-9.5, (b) AM-9.5-LDP and (c) AM-9.5-PD cultures. The hMSCs were cultivated for 7 days under serum- and xeno-free conditions. Samples from the indicated time points (day 1, day 3, day 5 and day 7) are shown. With respect to each microcarrier type, the upper images were captured by phase-contrast microscopy, whereas the lower images were captured by epifluorescence microscopy (live cells: green; dead cells: red). Scale bar of all images is 100 µm.

FIG. 4 shows a thermal response of the microcarriers according to one embodiment below. FIG. 4a shows volume and (b) surface area increase of thermoresponsive microcarriers upon cooling from 37° C. to room temperature. Microcarriers were suspended in water (black bars) or cell culture medium (white bars), and the changes in volume and surface area were determined after 10 min of cooling. (c) shows the rate of surface area increase of microcarrier upon cooling from 37° C. to room temperature when suspended in cell culture medium. Each data point shows the average ±s.d. of 10 microcarriers.

FIG. 5 is a diagram showing the synthesis of polydopamine-coated (112) thermoresponsive microsphere (AM-9.5-PD) or poly(DOPA)-coated (114) thermoresponsive microspheres (AM-9.5-LDP, AM-3.8-LDP and AM-3.8-70-LDP).

FIG. 6 shows the thermogravimetric analysis of thermoresponsive microcarriers.

FIG. 7 shows a number of FTIR spectra of seven thermoresponsive microcarriers represented by (a) AM-9.5, (b) AM-3.8, (c) AM-3.8-70, (d) AM-9.5-LDP, (e) AM-3.8-LDP, (f) AM-3.8-70-LDP and (g) AM-9.5-PD.

FIG. 8 shows a number of carbon (C) 1s x-ray photoelectron spectroscopy (XPS) spectra of seven microcarriers represented by (a) AM-9.5, (b) AM-3.8, (c) AM-3.8-70, (d) AM-9.5-LDP, (e) AM-3.8-LDP, (f) AM-3.8-70-LDP and g) AM-9.5-PD.

FIG. 9 shows a number of nitrogen (N) 1s x-ray photoelectron spectroscopy (XPS) spectra of seven microcarriers represented by (a) AM-9.5, (b) AM-3.8, (c) AM-3.8-70, (d) AM-9.5-LDP, (e) AM-3.8-LDP, (f) AM-3.8-70-LDP and (g) AM-9.5-PD.

FIG. 10 shows a number of oxygen (O) 15 x-ray photoelectron spectroscopy (XPS) spectra of seven microcarriers represented by (a) AM-9.5, (b) AM-3.8, (c) AM-3.8-70, (d) AM-9.5-LDP, (e) AM-3.8-LDP, (f) AM-3.8-70-LDP and (g) AM-9.5-PD.

FIG. 11 shows hMSC performance in cultures of (a) AM-3.8 microcarriers and (b) AM-3.8-LDP microcarriers for 7 days under serum- and xeno-free conditions. Samples from the indicated time points (day 1, day 3, day 5 and day 7) are shown. In each panel, the images on the left were captured by phase-contrast microscopy, whereas the images on the right were captured by epifluorescence microscopy (live cells: green; dead cells: red). FIG. 11c shows the boxed regions of FIG. 11a while FIG. 11d shows the boxed regions of FIG. 11b. Scale bars: 100 µm (panels a and b), 10 µm (panels c and d, left-hand), and 5 µm (panel d, right-hand).

FIG. 12 shows hMSC performance in cultures of (a) AM-3.8-70 microcarriers and (b) AM-3.8-70-LDP microcarriers for 7 days under serum- and xeno-free conditions. Samples from the indicated time points (day 1, day 3, day 5 and day 7) are shown. In each panel, the images on the left were captured by phase-contrast microscopy, whereas the images on the right were captured by epifluorescence microscopy (live cells: green; dead cells: red). FIG. 12c shows the boxed regions of FIG. 12a while FIG. 12d is a bar graph showing the total number of live cells per well which was determined by cell counting at the indicated time points (x-axis). The bars show the average±s.d. (n=4).

FIG. 13 is a number of bar graphs showing (a) the percentages of hMSCs harvested by after a temperature shift from 37° C. to 20° C. (compared to cell numbers harvested in parallel by trypsinization, which were set to 100%). Before harvesting, hMSCs were cultivated for 7 days with the indicated microcarriers, (b) numbers of hMSCs that were cultivated for 24 days with AM-3.8 (grey curve) and AM-3.8-LDP (black curve) microcarriers and (c) percentages of hMSCs that were harvested at the indicated time points (continuously up-scaled long-term cultures) from AM-3.8 (white bars) or AM-3.8-LDP (black bars) microcarriers by trypsinization (100%) or after a temperature shift to 20° C.

FIG. 14 shows the morphology of re-plated cells and colony-forming efficiency of hMSCs harvested from AM-3.8 or AM-3.8-LDP microcarriers. After 21 days of cultivation with AM-3.8 or AM-3.8-LDP microcarriers, cells were harvested by trypsinization (panels a and b) or after a temperature shift (panels d and e) and imaged after re-plating into multi-well plates. FIG. 14c shows the numbers of rounded up cells derived from AM-3.8-LDP cultures that were re-plated into multi-well plates after 21 days of cultivation on AM-3.8-LDP microspheres and then harvested by trypsinization or after a temperature shift. FIG. 14f shows the numbers of colonies (colony-forming unit-fibroblast (CFU-F) assay) after hMSCs were cultivated for 21 days in AM-3.8 or AM-3.8-LDP cultures and then harvested by trypsinization or after a temperature shift.

FIG. 15 shows a number of images of the marker expression determined by immunostaining. hMSCs were harvested after long-term expansion for 21 days on (a) AM-3.8 and (b) AM-3.8-LDP microspheres and were re-plated, and immunostained for CD44, CD14 and CD19 (green; cell nuclei: blue) after harvesting. Scale bars: 100 µm.

FIG. 16 shows a (a) FACS analysis with antibodies against the markers indicated. Cells were incubated either with individual fluorochrome-conjugated antibodies, or a mixture of fluorochrome-conjugated antibodies against CD34, CD11b, CD19, CD45 and HLA-DR. The percentages of positive cells (dark grey histograms) are indicated. Cells were also incubated under the same conditions without any antibodies, and the FACS results obtained with these cells are shown by the light grey histograms. hMSCs being differentiated into (b) adipogenic, (c) osteogenic and (d) chondrogenic lineages, and were stained as indicated or were left unstained, and imaged by phase contrast microscopy. The expression of lineage-specific genes was determined by qPCR (for full gene names see Table 1). Scale bars: 30 µm (b), 50 µm (c), and 100 µm (d).

DETAILED DESCRIPTION OF DRAWINGS

Referring to FIG. 1, FIG. 1 shows a schematic illustration of a number of thermoresponsive microspheres (100) for cell seeding (step 2), expansion and subsequent thermally-induced cell detachment at 20° C. (104). As shown in FIG. 1, cell seeding occurs (step 2) and a layer of cells (102) is attached onto the microsphere (100) and upon a temperature reduction (step 4), the expansion of the microsphere is due to the ingress of water to form the expanded microsphere (104). The detachment of the cells (104) from the microsphere surface could then come from the change in volume and surface area of the microsphere (100).

EXAMPLES

Non-limiting examples of the invention will be further described in greater detail by reference to specific Examples, which should not be construed as in any way limiting the scope of the invention.

Materials and Methods

All reagents for microcarrier synthesis and the stains for the differentiation procedures were purchased from commercial sources; Sigma Aldrich (St. Louis, Missouri, United States), Merck Millipore (Bayswater, Victoria, Australia), 1st BASE (Selangor, Malaysia) and Wako Pure Chemical Industries, Ltd. (Tokyo, Japan) and used as received.

Microcarrier Characterization

X-ray photoelectron spectroscopy (XPS) analysis was conducted on a VG ESCALAB MKII spectrometer. Fourier transform infrared (FT-IR) spectra were recorded on a Digilab FTS 7000 series spectrometer equipped with a MTEC-300 photoacoustic detector. Thermogravimetric analyses (TGA) were performed on a Perkin Elmer Pyris 1 thermogravimetric analyzer. The samples were heated at 10° C. $\min^{-1}$ from 25° C. to 700° C. using air for the carrying gas and $N_2$ for the protective gas.

Determination of Thermal-Induced Microcarrier Changes

Microcarriers were suspended in water or cell culture medium, and imaged by light microscopy at 37° C. and after reducing the temperature to room temperature. The diameters of the microcarriers were measured from the micrographs by using Image J software. Based on the measured microcarrier diameters, their volumes and surface areas were calculated (see Example 3 for the details).

Initial Expansion and Pooling of hMSCs

Passage 1 (P1) bone marrow hMSCs (cat-no. AH005-F) from different donors were purchased from DV Biologics (Costa Mesa, California, USA). hMSCs were expanded in MSC NutriStem XF complete medium (Biological Industries, Kibbutz Beit Haemek, Israel) containing MSC NutriStem XF Supplement Mix (Biological Industries, Kibbutz Beit Haemek, Israel) and penicillin-streptomycin. All components of this complete serum-free medium were defined and from non-xenogenic origin. This medium was used for all experiments, unless otherwise indicated. hMSCs were expanded until P2 in T75 flasks coated with MSC attachment solution (Biological Industries, Kibbutz Beit Haemek, Israel), and harvested with recombinant trypsin (Biological Industries, Kibbutz Beit Haemek, Israel) at about 90% confluency. P2 hMSCs from three different donors were pooled and cryopreserved; such pooled cells were used in all subsequent experiments.

hMSC Cultivation on Thermoresponsive Microcarriers

Prior to cell seeding, thermoresponsive microcarriers were washed with phosphate buffered saline (PBS) and equilibrated with MSC NutriStem XF complete medium for 1 hour. The microcarriers were then added to 24-well ultra-low attachment plates (Corning, New York, USA), and the microcarrier surface area was adjusted to 1.0 $cm^2$ per well. Pooled hMSCs were seeded onto the different thermoresponsive microcarriers at a density of 5000 cells $cm^{-2}$, and the final volume of MSC NutriStem XF complete medium was adjusted to 800 µL per well. The plates were transferred to a shaker 2 hour after cell seeding, and shaking was performed consistently throughout cultivation at 30 rpm. For removal of non-attached cells, the microcarriers were allowed to settle after 24 hours, and 600 µL of medium were removed from each well and replenished with fresh medium three times. Subsequent medium changes were performed every two days by exchanging 600 µL of medium per well for fresh MSC NutriStem XF complete medium. The viability of hMSCs attached to thermoresponsive microcarriers was evaluated by staining the cells with LIVE/DEAD Viability/Cytotoxicity Assay Kit (Molecular Probes, Eugene, Oregon). The numbers of microcarriers remained unchanged during cultivation periods of 7 days or less.

Scalable Expansion

AM-3.8 (control) and AM-3.8-LDP microcarriers were prepared as defined herein, and irradiated with UV light overnight before use. The microcarriers were added to 24-well ultra-low attachment plates (microcarrier surface area =1 $cm^2$ per well, which corresponded to 1 mg of microcarriers per well). Freshly thawed cryopreserved cells were seeded at a density of 5000 cells per well. MSC NutriStem XF medium was used for cultivation with shaking, and non-attached cells were removed as described earlier. Medium was exchanged every 2 days. Cell cultures were expanded by bead-to-bead transfer and fresh microcarriers were added at intervals of 4 days. 0.5 mg per well of fresh microcarriers (i.e. 50% of the original amount) was each added on day 4 and day 8. Thus, 2 mg of microcarriers per well was present from day 8 onwards. These were transferred on day 12 to a 6-well ultra-low attachment plate in order to avoid overcrowding. 2 mg of fresh microcarriers per well was added after transfer, which resulted in a total microcarrier amount of 4 mg per well (6-well plate) on day 12. 2 mg of microcarriers per well was each added on day 16 and day 20. This resulted in a total microcarrier amount of 8 mg per well from day 20 onwards. Although this expansion process was theoretically not limited, no further beads were added after day 20, and the cells were harvested after this time point for further analyses. To determine cell numbers during the expansion period, cells from parallel cultures were harvested every 4 days by trypsinization or cold treatment, as described below. Four replicates were analyzed per time point for each type of microcarriers.

Determination of Cell Numbers and Cell Yield at 20° C.

To determine cell numbers, the microcarriers were washed three times with PBS and then treated with recombinant trypsin (Biological Industries, Kibbutz Beit Haemek, Israel) for 30 minutes at 37° C. at 300 rpm on a thermomixer (Eppendorf, Hamburg, Germany). Total cell numbers and the numbers of viable cells were determined with a ViCell XR cell counter (Beckman Coulter, California, USA). All calculations were based on the number of viable cells.

When thermally induced cell detachment was evaluated, the cell numbers were always determined in parallel by enzymatic detachment as described herein. For thermal-induced cell detachment, the microcarriers were washed three times with PBS, and then incubated in cell culture medium at 20° C. for 120 minutes at 300 rpm on a thermomixer (Eppendorf, Hamburg, Germany). Total cell numbers and the number of viable cells were determined with a ViCell XR cell counter. The cell yield at 20° C. was calculated in the following way: cell yield (%)=[(number of viable cells obtained at 20° C.)/(number of viable cells obtained by trypsinization)]×100%.

Determination of Cell Morphology After Re-Plating hMSCs harvested from AM-3.8 and AM-3.8-LDP microcarriers by trypsinization or thermal detachment were reseeded onto 24-well tissue culture plates coated with MSC attachment solution at a density of 2000 cells $cm^{-2}$. After incubation for 24 hours, the cells were fixed with 3.7% formaldehyde/PBS for 10 minutes, and immunostained with an antibody against vimentin or stained with rhodamine phalloidin (Life Technologies, Carlsbad, California, USA). Nuclei were stained with 4',6-diamidino-2-phenylindole (DAPI). To determine the percentage of rounded cells, 10 images from each experiment were analyzed using ImageJ software.

Colony-Forming Unit-Fibroblast (CFU-F) Assay hMSCs harvested from AM-3.8 or AM-3.8-LDP microcarriers by thermal detachment on day 21 were resuspended at a final concentration of 150 cells $mL^{-1}$ in DMEM-low glucose medium (Life Technologies, Carlsbad, California, USA) with 10% MSC-qualified fetal bovine serum (Life Technologies, Carlsbad, California, USA), 2 mM L-glutamine and penicillin/streptomycin. The suspension was seeded into 35 mm dishes (1 mL per dish; 3 replicates each), and the cells were cultivated for 14 days. After staining with 0.5% crystal violet solution (Sigma Aldrich, St. Louis, MO, USA), the colonies were imaged with a ChemiDoc XRS system (BioRad Laboratories Inc., Hercules, California, USA), and the number of colonies was determined by using the Quantity One 1-D analysis software (BioRad Laboratories Inc., Hercules, California, USA).

Immunophenotyping hMSCs were expanded by bead-to-bead transfer with AM-3.8 and AM-3.8-LDP microcarriers as described herein. Cells were harvested from parallel cultures (4 replicates each) on day 21 after a temperature shift. For immunostaining, detached cells were re-seeded onto 24-well plates coated with MSC attachment solution (Biological Industries, Kibbutz Beit Haemek, Israel). The cells were grown to confluency and then fixed with 3.7% formaldehyde/PBS for 1 hour. Subsequently, the cells were washed and stained with antibodies specific for CD44, CD14 and CD19 from Merck Millipore (Billerica, Massachusetts, USA) Human Mesenchymal Stem Cell Characterization Kit following manufacturer's instructions.

Fluorescence-activated cell sorting (FACS) was performed with the BD Stemflow Human hMSC Analysis Kit (BD Biosciences, Franklin Lakes, New Jersey, USA). hMSCs harvested by a temperature shift after 21 days of expansion were fixed with 4% paraformaldehyde/PBS for 30 minutes at room temperature, and washed with PBS. The cells were then incubated with the fluorochrome-conjugated antibodies provided in the kit for 30 minutes at room temperature. The kit contained individual fluorochrome-conjugated antibodies with respect to CD44, CD73, CD90 and CD105 (hMSC markers), and a mixture of fluorochrome-conjugated antibodies against CD11b, CD19, CD34, CD45 and HLA-DR (control for expression of non-hMSC markers). Cells were incubated with antibodies (dark grey histograms in FIG. 16a) and without antibodies (light grey histograms in FIG. 16a) under otherwise the same conditions. The percentages of positive cells (dark grey histograms in FIG. 16a) are indicated. Cells were also incubated under the same conditions without any antibodies, and the FACS results obtained with these cells are shown by the light grey histograms (FIG. 16a). Subsequently, the cells were washed with PBS, and analyzed with a LSRII flow cytometry analyzer (BD Biosciences, Franklin Lakes, New Jersey, USA).

Osteogenic, Adipogenic and Chondrogenic Differentiation hMSCs were harvested from AM-3.8-LDP microcarriers by thermal induction after expansion for 21 days. Following long-term expansion, hMSCs were differentiated into (FIG. 16b) adipogenic, (FIG. 16c) osteogenic and (FIG. 16d) chondrogenic lineages, and were stained as indicated or were left unstained and imaged by phase contrast microscopy. The differentiation was performed with StemPro Complete Osteogenesis Differentiation medium, StemPro Complete Adipogenesis Differentiation medium or StemPro Complete Chondrogenesis medium (Life Technologies, Carlsbad, California, USA) according to standard procedures. Histochemical staining of differentiated samples was also performed according to standard procedures. Details on differentiation and histochemical staining procedures are described in Example 8.

RNA Extraction and Quantitative Real-Time Reverse Transcription Polymerase Chain Reaction (qPCR)

Total RNA was extracted using RNeasy Mini Kit (Qiagen Singapore Pte Ltd, Singapore). The RNA concentration was determined using a NanoDrop 2000 spectrophotometer (Thermo Fisher Scientific, Waltham, Massachusetts, USA). The total RNA was subjected to DNase treatment before use. Total RNA was converted to cDNA using the SuperScript III First-Strand Synthesis System (Life Technologies, Carlsbad, California, USA). qPCR was performed with Bio-Rad (Hercules, California, USA) CFX-96 qPCR System with the following program: 95° C. for 10 minutes for 1 cycle, followed by 95° C. for 15 seconds and 60° C. for 1 minutes for 40 cycles. The melting curve program was run by performing a gradual temperature increment of 0.5° C./30 s from 40° C. to 95° C. Primer pairs used and amplicon sizes are provided in Table 1. The qPCR data were analyzed using Microsoft Office Excel 2010. All results on marker gene expression were normalized to glyceraldehyde-3-phosphate dehydrogenase (GAPDH) expression levels.

TABLE 1

Markers used for qPCR.

| Acronym/Gene ID Description | Primer Pairs | Amplicon Size (bp) |
|---|---|---|
| ACAN/ACAN Aggrecan | F 5' ACTTCCGCTGGTCAGATGGA 3' (SEQ ID NO: 1)<br>R 5' TCTCGTGCCAGATCATCACC 3' (SEQ ID NO: 2) | 111 |
| CEBPA/CEBPA CCAAT/enhancer binding protein (C/EBP), alpha | F 5' CGGCAACTCTAGTATTTAGGATAACCTT 3' (SEQ ID NO: 3)<br>R 5' CACGATTTGCTCCCCCTACTC 3' (SEQ ID NO: 4) | 88 |
| COLX/COL10A1 Collagen, type X, alpha 1 | F 5' CAAGGCACCATCTCCAGGAA 3' (SEQ ID NO: 5)<br>R 5' AAAGGGTATTTGTGGCAGCATATT 3' (SEQ ID NO: 6) | 70 |
| COL1/COL1A1 Collagen, type 1, alpha 1 | F 5' CAGCCGCTTCACCTACAGC 3' (SEQ ID NO: 7)<br>R 5' TTTTGTATTCAATCACTGTCTTGCC 3' (SEQ ID NO: 8) | 83 |
| COMP/COMP Cartilage oligomeric matrix protein | F 5' GGAGATCGTGCAGACAATGA 3' (SEQ ID NO: 9)<br>R 5' GAGCTGTCCTGGTAGCCAAA 3' (SEQ ID NO: 10) | 147 |
| FABP4/FABP4 Fatty acid binding protein 4, adipocyte | F 5' TGGTGGAATGCGTCATGAAA 3' (SEQ ID NO: 11)<br>R 5' CAACGTCCCTTGGCTTATGC 3' (SEQ ID NO: 12) | 70 |
| GAPDH/GAPDH Glyceraldehyde-3-phosphate dehydrogenase | F 5' GAAGGTGAAGGTCGGAGT 3' (SEQ ID NO: 13)<br>R 5' GAAGATGGTGATGGGATTTC 3' (SEQ ID NO: 14) | 226 |
| OPN/SPP1 Secreted phosphoprotein 1, bone sialoprotein 1, osteopontin | F 5' GCCAGTTGCAGCCTTCTCA 3' (SEQ ID NO: 15)<br>R 5' AAAGCAAATCACTGCAATTCTCAT 3' (SEQ ID NO: 16) | 74 |
| OSX/SP7 Sp7 transcription factor, osterix | F 5' TCCCTGCTTGAGGAGGAAGTT 3' (SEQ ID NO: 17)<br>R 5' CACGCTGCCGTCAGCAT 3' (SEQ ID NO: 18) | 62 |
| PPARG/PPARG Peroxisome proliferator-activated receptor gamma | F 5' GAGGGCGATCTTGACAGGAA 3' (SEQ ID NO: 19)<br>R 5' TCTCCCATCATTAAGGAATTCATG 3' (SEQ ID NO: 20) | 78 |
| RUNX2/RUNX2 Runt-related transcription factor 2 | F 5' CGTGGCCTTCAAGGTGGTA 3' (SEQ ID NO: 21)<br>R 5'-CGGAGCTCAGCAGAATAATTTTC-3' (SEQ ID NO: 22) | 96 |
| SOX9/SOX9 SRY (sex determining region Y)-box 9 | F 5' AGTACCCGCACTTGCACAA 3' (SEQ ID NO: 23)<br>R 5' CTCGTTCAGAAGTCTCCAGAGCTT 3' (SEQ ID NO: 24) | 68 |

The table lists all markers used for qPCR and their names, acronyms and gene IDs, which follow the nomenclature of the HUGO Gene Nomenclature Committee (HGNC) (http://www.genenames.org/). The primer pairs used for qPCR (F: forward, R: reverse), and amplicon sizes in base pairs (bp) are shown.

Statistical Analysis

All calculations and the unpaired t-test were performed with Microsoft Office Excel 2010. Normal distribution of the data was confirmed using SigmaStat 3.5 (Systat Software Inc., Chicago, Illinois, USA). All values were expressed as mean±standard deviation (s.d.) (n=3).

Example 1

A general synthetic method using a free radical polymerization within a water-in-oil (w/o) microemulsion system was developed for the synthesis of thermoresponsive microcarriers (FIG. 2). In this process, the feed solution contained the monomer of the thermoresponsive component N-isopropylacrylamide (IPAAm) and monomers with functional groups that could promote cell attachment or permit further functionalization: methacrylic acid (MA), (3-acrylamidopropyl)trimethylammonium chloride (APTACl), N-[3-(dimethylamino)propyl]methacrylamide (DMAPM) or 2-aminoethyl methacrylate hydrochloride (AMHCl). The monomers were polymerized with the crosslinker N,N'-methylenebis(acrylamide) (MBA) in a water/toluene microemulsion system. Free radical polymerization was initiated at room temperature with ammonium persulfate/N,N,N',N'-tetramethylethylenediamine or at higher temperatures with the azo initiator 2,2'-azobis[2-(2-imidazolin-2-yl)propane] dihydrochloride. Microcarriers produced in this way were sieved, and the fraction in the size range of 125-177 μm was used.

Synthesis of AM-3.8, AM-3.8-50 and AM-3.8-70 Microcarriers

For synthesis of AM-3.8 microcarriers, toluene (50 g) and SPAN 85 (3.0 g) were stirred at room temperature and purged with argon for 30 minutes in a 100-mL three-necked flask equipped with a mechanical stirrer. A solution of N-isopropylacrylamide (1.297 g, 11.46 mmol), 2-aminoethyl methacrylate hydrochloride (0.079 g, 0.48 mmol), N,N'-methylenebis(acrylamide) (0.10 g, 0.65 mmol) and ammonium persulfate (0.10 g, 0.44 mmol) in water (4.4 mL) was purged with argon for 5 minutes and syringed into the stirred solution of toluene/SPAN 85. The milky suspension was stirred at room temperature under argon for 15 min at 300 rpm, and N,N,N',N'-tetramethylethylenediamine (0.02 mL) was added. After 5 hours of reaction at room temperature, microcarriers were collected via filtration using a 100-μm nylon mesh filter. The microcarriers were washed with acetone (60 mL) and dried at room temperature under vacuum overnight (1.2 g). The product (AM-3.8 microcarrier) was fractioned by sieving through to obtain the 125 to 177 μm fraction (47%).

For synthesis of AM-3.8-50 and AM-3.8-70 microcarriers, they were synthesized in similar ways as AM-3.8 microcarriers, with the exception that the feed solution contained 2,2'-azobis[2-(2-imidazolin-2-yl)propane]dihydrochloride (0.10 g, 0.39 mmol) instead of ammonium persulfate and N,N,N',N'-tetramethylethylenediamine. A solution of N-isopropylacrylamide, 2-aminoethyl methacrylate hydrochloride, N,N'-methylenebis(acrylamide) and 2,2'-azobis[2-(2-imidazolin-2-yl)propane]dihydrochloride in water was purged with argon for 5 minutes and syringed into the stirred solution of toluene/SPAN 85. The milky suspension of the feed solution in toluene/SPAN 85 was heated for 2 hours after stirring, to 50° C. and 70° C. for AM-3.8-50 and AM-3.8-70 respectively, before cooling and filtration. The yield of the 125-177 μm fraction was 34% and 48% for AM-3.8-50 and AM-3.8-70 respectively.

Synthesis of MA-9.5, AP-9.5, DM-9.5, AM-9.5, AM-9.0 and AM-3.6 Microcarriers

These microcarriers were synthesized in similar ways as AM-3.8 microcarriers. In the case of MA-9.5, 1.5 g of SPAN 85 was used. The feed composition for the different microcarriers is shown in Table 2. The feed solution was adjusted to pH 9.0 (MA-9.5) or pH 2.0 (DM-9.5). The reaction time before microcarrier collection was 5 hours (AM-9.5, AM-9.0, AM-3.6), 17 hours (MA-9.5), 18 hours (AP-9.5) or 19 hours (DM-9.5). MA-9.5 microcarriers were washed with 1 N aqueous HCl overnight, before washing with deionized water and drying. The 125-177 μm fraction of microcarrier particles was 20% (MA-9.5, AP-9.5, DM-9.5), 37% (AM-3.6), 40% (AM-9.0) or 60% (AM-9.5).

Four different types of thermoresponsive microcarriers (MA-9.5, AP-9.5, DM-9.5 and AM-9.5; see Table 2) with different functional groups (e.g. carboxylic acid, quaternary ammonium, tertiary amine or primary amine) were produced. The thermal response between 37° C. and room temperature was determined in both water and cell culture medium. Of these four types of microcarriers, the microcarrier with the primary amine functional group (AM-9.5) showed the largest percentage of volume and surface area increase (FIG. 4), especially when suspended in cell culture medium (158±11% and 88±5%, respectively). The volume and surface area increase in water was smaller (40±6% and 25±3%, respectively) as the primary amine functional group remained positively charged in pH neutral water, and would thus retain more water molecules at 37° C. MA-9.5, AP-9.5 and DM-9.5 microcarriers exhibited smaller thermal responses in both water and cell culture media as their ionized functional groups attracted more water at 37° C.

TABLE 2

The feed composition, reaction temperature and catecholamines that were used for the synthesis.

| Microcarrier | Feed composition (mol %) | | | | | | Temperature | Coating |
| | IPAAm | MA | APTACl | DMAPM | AMHCl | MBA | | |
| --- | --- | --- | --- | --- | --- | --- | --- | --- |
| MA-9.5 | 85.3 | 9.5 | | | | 5.2 | 25 | |
| AP-9.5 | 85.3 | | 9.5 | | | 5.2 | | |
| DM-9.5 | 85.3 | | | 9.5 | | 5.2 | | |
| AM-9.5 | 85.3 | | | | 9.5 | 5.2 | | |
| AM-9.0 | 81.1 | | | | 9.0 | 9.9 | | |
| AM-3.6 | 86.6 | | | | 3.6 | 9.8 | | |
| AM-3.8 | 91.1 | | | | 3.8 | 5.1 | | |
| AM-3.5-50 | 91.1 | | | | 3.8 | 5.1 | 50 | |
| AM-3.8-70 | 91.1 | | | | 3.8 | 5.1 | 70 | |
| AM-9.5-PD | 85.3 | | | | 9.5 | 5.2 | 25 | Dopamine |
| AM-9.5-LDP | 85.3 | | | | 9.5 | 5.2 | | DOPA |
| AM-3.8-LDP | 91.1 | | | | 3.8 | 5.1 | | |
| AM-3.8-70-LDP | 91.1 | | | | 3.8 | 5.1 | 70 | |

The table shows the feed composition, reaction temperature and catecholamines used for the 13 microcarriers that were synthesized and the respective coatings that were utilized.

To further increase the thermal response, the composition of the microcarrier containing the primary amine functional group was varied, which resulted in AM-9.0, AM-3.6 and AM-3.8 microcarriers (Table 2). It was found that a larger thermal response could be attained by decreasing the quantity of the primary amine functional group to 3.8 mol % and maintaining the crosslinker quantity at 5.1 mol % (Table 2 and FIG. 4—compare AM-3.8 with AM-9.5, AM-9.0 and AM-3.6). A higher synthesis temperature of 50° C. or 70° C. respectively, resulted in a smaller thermal response (Table 2 and FIG. 4—compare AM-3.8-50 and AM-3.8-70 with AM-3.8) due to a higher degree of crosslinking.

Example 2

Coating with Polymerized
L-3,4-dihydroxyphenylalanine (DOPA) or
Dopamine

To generate AM-3.8-LDP microcarriers, 0.007 g AM-3.8 microcarriers were washed four times with phosphate buffered saline (PBS). In the last wash, 0.5 mL of the PBS solution was pipetted out, and a solution of L-3,4-dihydroxyphenylalanine (DOPA) (0.5 mL, 2 mg mL$^{-1}$) in 10 mM Tris HCl buffer (pH 8.5) was added (final volume: 1 mL) (step 8). The microcarriers were then shaken at room temperature under air for 22 hours. The reaction mixture was removed after centrifugation at 13000 rpm for 30 seconds, and the coated microcarriers were washed with deionized water. The microcarriers were dried at room temperature under vacuum overnight.

AM-9.5-LDP and AM-3.8-70-LDP microcarriers were synthesized via a similar method with AM-9.5 and AM-3.8-70 microcarriers respectively. An overview of the polymer coated microcarriers is provided in FIG. 5.

To generate AM-9.5-PD microcarriers, AM-9.5 microcarriers (0.020 g) were shaken in 0.5 mL dopamine hydrochloride solution (2 mg mL$^{-1}$ in 10 mM potassium phosphate buffer, pH 8.2) (step 6) and in a 1.5-mL centrifuge tube at room temperature under air for 20 hours. The solution reaction mixture was pipetted out (after centrifugation at 14680 rpm for 5 minutes), and the coated microcarriers were washed with deionized water and acetone. The microcarriers were dried at room temperature under vacuum overnight.

Coating with the polymerized catecholamines, dopamine and L-3,4-dihydroxyphenylalanine (DOPA), have been shown to improve the performance of various mammalian cell types on synthetic substrates. It was shown in earlier reports that coating with polymerized DOPA would allow synthetic substrates to be compatible for the large-scale expansion of human pluripotent stem cells under defined serum-free conditions. As the goal was the synthesis of thermoresponsive microcarriers that can be applied under such similar conditions, the microcarriers with large thermal responses (AM-9.5, AM-3.8 and AM-3.8-70) were coated with polymerized dopamine or DOPA (Table. 2 and FIG. 5; AM-9.5-PD, AM-9.5-LDP, AM-3.8-LDP and AM-3.8-70-LDP). This treatment decreased the thermal response and when compared to the respective uncoated microcarriers, there was a 14 to 44% reduction on the volume increase, and a 13 to 39% reduction on the surface area increase (FIG. 4).

Example 3

Calculation of Microcarrier Volume and Surface Area

Microcarrier volume increase was calculated using the following equation:

$$\text{Volume increase of microcarrier (\%)} = \frac{V_{RT} - V_{37°C.}}{V_{37°C.}} \times 100\%$$

where $V_{RT}$ and $V_{37°C.}$ represent the volume of the microcarrier at room temperature and 37° C., respectively, and the volume of the microcarrier was calculated using the following equation:

$$V = \frac{4}{3}\pi\left(\frac{d}{2}\right)^3,$$

where d represents the diameter of the microcarrier. The percent volume increase was calculated as mean±standard deviation (S.D.) for ten microcarriers.

Microcarrier surface area increase was calculated using the following equation:

$$\text{Surface area increase of microcarrier (\%)} = \frac{SA_{RT} - SA_{37°C.}}{SA_{37°C.}} \times 100\%$$

where $SA_{RT}$ and $SA_{37°C.}$ represent the surface area at room temperature and 37° C., respectively, and the microcarrier surface area was calculated using the following equation:

$$SA = 4\pi\left(\frac{d}{2}\right)^2.$$

The percent surface area increase was calculated as mean ±standard deviation (S.D.) for ten microcarriers.

Example 4

Physico-Chemical Characterization of the Seven Microcarriers

Thirteen microcarriers were synthesized and only seven (7) microcarriers were chosen for further characterization and cell culture studies. AM-9.5, AM-3.8, AM-9.5-LDP, AM-3.8-LDP and AM-9.5-PD were selected based on their large thermal response in cell culture medium, and potentially improved cytocompatibility after coating with polymerized catecholamines. AM-3.8-70 and AM-3.8-70-LDP were selected as a higher degree of crosslinking might improve cell adhesion and growth.

Thermogravimetric analysis revealed that the seven selected thermoresponsive microcarriers were stable up to 100° C. (FIG. 6). These microcarriers contained about 4 to 8% volatile components (e.g. water) as confirmed by the weight loss upon heating to 100° C. The Fourier-transform infrared (FTIR) spectra of the different microcarriers were similar (FIG. 7). The presence of the secondary amide group was confirmed by the presence of the amide N—H stretch at 3280 cm$^{-1}$ and the amide C=O stretch at 1666 cm$^{-1}$. The peaks at 2970, 2924 and 2873 cm$^{-1}$ were assigned to asymmetric C—H stretching vibrations, while the peak at 1366 cm$^{-1}$ was attributed to symmetric C–H deformation vibration.

X-ray photoelectron spectroscopy (XPS) was employed to track the changes in the surface characteristics of the microcarriers upon coating with polymerized DOPA or dopamine (FIGS. 8 to 10). The carbon (c) 1s XPS spectra were curve-fitted into 3 peak components with binding energies at ~284.5 eV, 286.0 eV, and 287.6 eV, which were attributed to the C—C, C—O and C—N, and O—C=O and N—$\underline{C}$=O species, respectively (FIG. 8 and Table 3). Coating was associated with an increase in the $\underline{C}$—C peak. This arose from the presence of the aromatic ring of the polymerized DOPA or dopamine. The nitrogen (N) 1s XPS spectra of microcarriers AM-9.5, AM-3.8 and AM-3.8-70 were deconvoluted into two components. Peaks at about 399.3 eV and 401.3 eV were assigned to —$\underline{N}$—C=O and —$\underline{N}^+H_3$ species, respectively (FIG. 9). After coating, the N 1s XPS spectra could be curve-fitted into three components with binding energies at about 398.4 eV, 399.3 eV and 401.5 eV. These were attributed to the —$\underline{NH}_2$, $\underline{N}$—C=O and —$\underline{N}^+$=C species, respectively (FIG. 9 and Table 4). The —$\underline{N}^+$=C species could arise from the imino functionality of polymerized DOPA or dopamine. The oxygen (O) 1s XPS spectra could be curve-fitted into two components. The peak at ~531.2 eV was ascribed to the C=$\underline{O}$ species, while the peak at ~532.9 eV was attributed to the C—$\underline{O}$ species, respectively (FIG. 10 and Table 5). Coating resulted in an increase in the deconvoluted C=$\underline{O}$ peak component. This was probably due to the presence of quinone moieties in polymerized DOPA or dopamine. Together, these results showed that coating altered the surface chemistry of the thermoresponsive microcarriers.

TABLE 3

Summary of the C 1s Area (%) for the 7 microcarriers

| Microcarrier | C 1s Area (%) | | |
| --- | --- | --- | --- |
| | 284.5 eV $\underline{C}$—C | 286.0 eV $\underline{C}$—O, $\underline{C}$—N | 287.6 eV O—$\underline{C}$=O, N—$\underline{C}$=O |
| AM-9.5 | 73.8 | 16.0 | 10.2 |
| AM-3.8 | 77.3 | 11.9 | 10.8 |
| AM-3.8-70 | 72.4 | 15.8 | 11.8 |
| AM-9.5-LDP | 82.0 | 10.0 | 8.0 |
| AM-3.8-LDP | 91.7 | 4.7 | 3.6 |
| AM-3.8-70-LDP | 82.4 | 10.2 | 7.4 |
| AM-9.5-PD | 83.7 | 9.5 | 6.8 |

TABLE 4

Summary of the N 1s Area (%) for the 7 microcarriers

| Microcarrier | N 1s Area (%) | | | |
| --- | --- | --- | --- | --- |
| | 398.4 eV —$\underline{N}H_2$ | 399.3 eV —$\underline{N}$—C=O | 401.3 eV —$\underline{N}^+H_3$ | 401.5 eV —$\underline{N}^+$=C |
| AM-9.5 | — | 78.2 | 21.8 | — |
| AM-3.8 | — | 96.5 | 3.5 | — |
| AM-3.8-70 | — | 97.1 | 2.9 | — |
| AM-9.5-LDP | 4.0 | 94.9 | — | 1.1 |
| AM-3.8-LDP | 2.9 | 95.6 | — | 1.5 |
| AM-3.8-70-LDP | 4.2 | 91.7 | — | 4.1 |
| AM-9.5-PD | 5.5 | 85.6 | — | 8.9 |

TABLE 5

Summary of the O 1s Area (%) for the 7 microcarriers

| Microcarrier | O 1s Area (%) | |
| --- | --- | --- |
| | 531.2 eV C=$\underline{O}$ | 532.9 eV C—$\underline{O}$ |
| AM-9.5 | 80.4 | 19.6 |
| AM-3.8 | 74.1 | 25.9 |
| AM-3.8-70 | 66.5 | 33.5 |
| AM-9.5-LDP | 85.7 | 14.3 |
| AM-3.8-LDP | 91.9 | 8.1 |
| AM-3.8-70-LDP | 88.2 | 11.8 |
| AM-9.5-PD | 84.8 | 15.2 |

Example 5 hMSC Performance on Thermoresponsive Microcarriers

The next series of experiments addressed the performance of hMSCs on the seven selected microcarriers. Bone marrow-derived hMSCs were cultivated under serum- and xeno-free conditions for seven days.

As shown in FIG. 11(a) AM-3.8 microcarriers have a weak red autofluorescence, which was quenched in AM-3.8-LDPs (refer to FIG. 11b) that were coated with polymerized DOPA and have a dark-brown color. Arrows point to spheroids, which were located between the microcarriers (panel a, left-hand images) and often appeared "hollow" or with a red core (panel a, days 5 and 7) on epifluorescence images due to internal cell death. Boxed regions were enlarged in panels (c) and (d). The few cells attached to AM-3.8 surfaces were rounded up (panel c, arrowheads). hMSCs spread on AM-3.8-LDP surfaces and were flat with a fibroblast-like morphology (panel d, arrowheads).

As shown in FIG. 12(a), AM-3.8-70 microcarriers have a weak red autofluorescence, which was quenched in AM-3.8-70-LDPs (refer to FIG. 12b) that were coated with polymerized DOPA and have a dark-brown color. In AM-3.8-70 cultures (FIG. 12a), microcarrier surfaces were devoid of cells and hMSCs formed spheroids. A spheroid that was located in the boxed area (a) is shown enlarged in panel (c) (left-hand image). Extensive spreading and growth of hMSCs on AM-3.8-70-LDP microcarriers led to the formation of hMSC/microcarrier complexes. Panel (c) (right-hand image) shows enlarged section of boxed area panel (b), where a hMSC "web" spreading along microcarrier surfaces. Scale bars: 100 μm. FIG. 12d shows the total number of live cells per well which was determined by cell counting at the indicated time points (x-axis). On day 7, the cell numbers in AM-3.8-70 (white bars) and AM-3.8-70-LDP (black bars) cultures were significantly different (asterisk; $P<0.05$).

hMSCs did not grow on the surfaces of uncoated AM-3.8 and AM-3.8-70 microcarriers (FIGS. 11a and 12a). The same applied to all microcarriers of the AM-9.5 class, which contained relatively high amounts of 2-aminoethyl methacrylate hydrochloride (AMHCI) (Table 2 and FIG. 3). In all of these cases, the hMSCs self-aggregated into spheroids, and during the whole cultivation period, only a few hMSCs were found on the microcarrier surfaces. These cells remained rounded up and were not spread on the microcarrier surface (FIG. 11c).

In contrast, hMSCs displayed attachment to and spreading on the surfaces of AM-3.8-LDP and AM-3.8-70-LDP microcarriers (FIGS. 11b and 12b). Spheroids were not observed in these cultures, and essentially all of the cells were attached to the microcarrier surfaces. Spreading of hMSCs along the surfaces of multiple microcarriers led to the formation of hMSC/microcarrier complexes (FIGS. 11d and 12c—see right panel). A steady increase in cell numbers occurred during the cultivation period whereby cells were growing on microcarrier surfaces, as in case of AM-3.8-70-LDP microcarriers (FIG. 12d). In contrast, spheroid-containing AM-3.8-70 cultures contained significantly lower cell numbers at later time points (FIG. 12d). Live/dead staining revealed the occurrence of cell death in spheroids at later time points (FIG. 11a). Only a few dead cells were observed in AM-3.8-LDP and AM-3.8-70-LDP microcarrier cultures, whereby cells were growing on the microcarrier surfaces (FIGS. 11b and 12b).

In summary, hMSC compatibility was only observed when the microcarriers contained relatively low amounts of AMHCI and when the microcarrier surfaces were coated with polymerized DOPA, as in case of AM-3.8-LDP and AM-3.8-70-LDP microcarriers. These microcarriers supported hMSC attachment, spreading, growth and survival under serum- and xeno-free conditions.

Example 6

Thermal Detachment

Next, the thermal-induced hMSC detachment was tested, and the yield of cells after 7 days of cultivation when the temperature was decreased from 37° C. to 20° C. was tabulated. Cells were always harvested in parallel by trypsinization, and the numbers obtained by trypsinization were set to 100%. A similar cell yield (99%) after a temperature shift to 20° C. (without trypsinization) was only obtained with AM-3.8-LDP microcarriers (FIG. 13a). The bars show the cell yield relative to that by trypsinization after the temperature shift to 20° C. (average±s.d.; n=4). The average percentages are indicated. The results show efficient thermal detachment from the AM-3.8-LDP microcarriers, to which hMSCs attached during cultivation (FIG. 11).

In contrast, the cell yield after the temperature shift (relative to trypsinization) was only 29% in case of AM-3.8-70-LDP microcarriers (FIG. 13a). Microscopic evaluation confirmed that thermal detachment was inefficient in this case, and many cells remained attached to the microcarriers after the temperature shift. The differences in thermal detachment efficiency between AM-3.8-LDP and AM-3.8-70-LDP microcarriers were consistent with the fact that the thermal-induced surface area and volume increase was much lower in case of AM-3.8-70-LDP microcarriers (FIG. 4).

Although in all other cases, cells did not attach to the microcarriers during cultivation (FIGS. 3, 11 and 12), the cell yield after the temperature shift appeared to be relatively low compared to trypsinization (FIG. 13a). This was due to the fact that the cells remained organized into spheroids after the temperature shift, and the number of individual cells was underestimated by cell counting. In contrast, trypsinization produced single-cell suspensions, where individual cells could be accurately counted.

Scalable Expansion

Thus far, the result showed that proper growth on microcarrier surfaces and efficient thermal detachment occurred only in case of AM-3.8-LDP microcarriers. Next, it was tested whether these microcarriers were suitable for scalable expansion under serum- and xeno-free conditions. Freshly thawed cryopreserved hMSCs were directly seeded on AM-3.8-LDP and AM-3.8 (control) microcarriers, and the cells were expanded for 24 days in a rocking bioreactor system (FIG. 13b). Regular up-scaling at 4-day intervals occurred during the cultivation period by adding new microcarriers and bead-to-bead transfer. In this way, the microcarrier surface area was increased 8-fold between day 1 and day 20 (FIG. 13b). In FIG. 13b, the asterisks indicate significant differences between cell numbers obtained with the different microcarriers. The x-axis shows the time scale (days) and the microcarrier surface area ($cm^2$) at each time point. During the cultivation period, the cultures were up-scaled at 4-day intervals.

In the AM-3.8 cultures, the average cell numbers slowly increased by ~30-fold from ~1600 on day 1 to ~48600 on day 24 (FIG. 13b; cell numbers were determined by trypsinization). This corresponded to a population doubling time of 159 hours. In AM-3.8-LDP cultures, the cells were exponentially growing at a faster rate (FIG. 13b), and in the continuously up-scaled system, no plateau phase was reached. The cells were harvested in the exponential phase after day 20 for follow-up assays. AM-3.8-LDP cultures had an average cell number of ~4000 on day 1 and ~499200 on day 24. This revealed an attachment efficiency of ~80% after seeding (5000 cells were seeded on day 0, and cells were counted on day 1 after removal of non-attached cells). Cell numbers increased ~125-fold between day 1 and day 24. This corresponded to a population doubling time of 92 hours. The thermal detachment efficiency was determined throughout the cultivation period, and was consistently in the range of about 90% in the case of AM-3.8-LDP microcarriers (FIG. 13c). In FIG. 13c, the relative percentages of viable cells obtained after the temperature shift are shown (average±s.d.; n=4). Asterisks indicate significant differences between AM-3.8 and AM-3.8-LDP cultures.

Example 7

Re-Plating and Colony-Forming Capacity

Subsequently, the performance of cells that had been re-plated after expansion on thermoresponsive microcarriers was attended to. For these experiments, hMSCs were expanded in AM-3.8-LDP and AM-3.8 (control) cultures. The cells were harvested on day 21 either by trypsinization or a temperature shift to 20° C., and re-plated into adhesion-coated tissue culture plates. After 24 hours, the cells were stained for F-actin or vimentin (red) and the cell nuclei were counterstained with DAPI (blue), and subsequently the cells were imaged (FIG. 14) The cells harvested from AM-3.8-LDP cultures were counted on 10 randomly selected images each. The average cell number harvested by trypsinization or a temperature shift was 21±7 and 28±6 per image, respectively. The results showed significantly lower (P<0.05) cell numbers obtained from enzymatic harvesting.

Furthermore, cells from AM-3.8-LDP and AM-3.8 cultures harvested by trypsinization did not display the typical elongated morphology (FIG. 14a and b). More than 40% of the cells derived from AM-3.8-LDP cultures were rounded up after trypsinization (FIG. 14c, white bar). Cells with an aspect ratio (length/width) of 2 or less were defined as a "rounded-up". The bars show the average±s.d.; 100 cells derived from 10 randomly selected images were counted in each case. The numbers of cells that remained rounded up were significantly higher after trypsinization (asterisk; 41% vs. 13%; P<0.05). In contrast, only ~13% of cells were rounded up when harvested after a temperature shift (FIG. 14c, black bar). The vast majority of cells harvested from AM-3.8-LDP cultures after a temperature shift displayed normal spreading and the characteristic fibroblast-like morphology (FIG. 14d and e; right). These results showed that enzymatic treatment had negative effects on the numbers of re-plated cells and on their spreading and morphology, in contrast to thermal detachment.

Cells derived from the spheroids that formed in AM-3.8 cultures displayed improved spreading when harvested after a temperature shift (FIG. 14d and e; left). However, in this case, the morphology was not elongated and fibroblast-like after re-plating, but was reminiscent of dendritic and epithelial cells. This might reflect differentiation processes occurring in spheroids. In summary, hMSCs that showed normal spreading and a fibroblast-like morphology were only obtained from AM-3.8-LDP cultures and harvesting by thermal detachment.

The colony-forming unit-fibroblast (CFU-F) assay was also performed where the colonies were obtained under all conditions (FIG. 14f). The number of CFU-Fs was significantly higher when cells were derived from AM-3.8-LDP cultures, as compared to AM-3.8 cultures. The lowest numbers of CFU-Fs were derived from trypsinized AM-3.8 cultures.

Example 8

Maintenance of the hMSC Immunophenotype and Multipotency During Long-Term Expansion Next, it was determined whether hMSCs maintained their characteristic immunophenotype during long-term expansion. hMSCs must express CD73, CD90 and CD105, and lack expression of CD45, CD34, CD14, CD11b, CD79α, CD19 and HLA-DR. CD44 is generally expressed by hMSCs. Cells harvested on day 21 by thermal detachment from AM-3.8-LDP cultures were analyzed by fluorescence-activated cell sorting (FACS). The hMSCs were fixed with 4% paraformaldehyde/PBS for 30 minutes at room temperature, and washed with PBS. The cells were then incubated with the fluorochrome-conjugated antibodies provided in the kit for 30 minutes at room temperature. The kit contained individual fluorochrome-conjugated antibodies with respect to CD90, CD44, CD73 and CD105 (hMSC markers). More than 98% of the cells showed expression of CD44, CD73, CD90 and CD105, whereas only ~0.03% of cells gave a positive result when a cocktail of antibodies against CD45, CD34, CD11b, CD19 and HLA-DR was applied (FIG. 16a). Immunostaining of hMSCs harvested on day 21 from AM-3.8 and AM-3.8-LDP cultures after a temperature shift confirmed that cells from both cultures were positive for CD44 and negative for CD14 and CD19 (FIG. 15).

In order to address the maintenance of multipotency, hMSCs were harvested from AM-3.8-LDP microcarriers by thermal induction after expansion for 21 days, and reseeded into a 12-well tissue culture plate at a density of 5000 cells $cm^{-2}$. Subsequently, cells were cultivated under conditions inducing adipogenic, osteogenic and chondrogenic differentiation. In the case of FIG. 16b adipogenic differentiation, they were incubated with 60% isopropanol for 5 minutes, and subsequently stained with Oil Red O. They were stained with 2% Alizarin Red S (Sigma Aldrich) solution (pH 4.2) in the case of FIG. 16c osteogenic differentiation. For FIG. 16d chondrogenic differentiation, hMSCs were harvested after 21 days of expansion from AM-3.8-LDP microcarriers by thermal induction and reseeded into a 1.5-mL Eppendorf tube at a density of $2.5 \times 10^5$ cells $mL^{-1}$ in MSC NutriStem XF medium and stained accordingly. Changes of cellular morphology and histochemical staining results were consistent with adipogenic, osteogenic and chondrogenic differentiation (FIG. 16b to d). Furthermore, the results revealed significant up-regulation of genes specific for adipogenic, osteogenic and chondrogenic lineages (FIG. 16b to d). The diagrams (right of FIG. 16b to d) display the fold change (y-axis) compared to undifferentiated hMSCs (average±s.d; n=3) and significant upregulation was indicated by asterisks (b) adipogenic markers: *P=8.38×10−6, P=1.80×10−6, *P=2.63×10−7, (c) osteogenic markers: *P=0.026, P=3.44×10−5, *P=5.40×10−5, (d) chondrogenic markers: *P=1.12×10−3, P=3.15×10−3, *P=2.72×10−8, **p=1.18×10−3, ***p=2.04×10−3). Together, these results confirmed maintenance of multipotency during long-term expansion and harvesting by thermal detachment.

The details are that the cells were incubated in MSC NutriStem XF medium for 2 hours. Nutristem MSC XF medium was replaced with pre-warmed StemPro Complete Osteogenesis Differentiation medium or StemPro Complete Adipogenesis Differentiation medium. After 21 days of differentiation, the cells were fixed. They were stained with 2% Alizarin Red S solution (pH 4.2) in the case of osteogenic differentiation. In the case of adipogenic differentiation, they were incubated with 60% isopropanol for 5 minutes, and subsequently stained with Oil Red O.

For chondrogenic differentiation, hMSCs were harvested after 21 days of expansion from AM-3.8-LDP microcarriers by thermal induction and reseeded into a 1.5-mL Eppendorf tube at a density of $2.5 \times 10^5$ cells $mL^{-1}$ in MSC NutriStem XF medium. The cells were then centrifuged at 400 g for 5 minutes to generate a tight pellet. The medium was removed, and pre-warmed Stem Pro Complete Chondrogenesis medium was gently added without disrupting the pellet. The pellets were harvested after 14 days of cultivation. Histological processing of the chondrogenic pellets was performed by the Advanced Molecular Pathology Laboratory at the Institute of Molecular and Cell Biology (IMCB, Agency for Science, Technology and Research, Singapore).

INDUSTRIAL APPLICABILITY

The microsphere of the present disclosure may be a thermoresponsive system that combines key features that are required for clinical applications of hMSCs. The microsphere may be suitable for the scalable expansion of hMSCs under defined serum- and xeno-free conditions. In addition to allowing expansion of hMSCs under fully defined conditions, as required for clinical applications, cell numbers can be increased at least 130-fold. The potential for producing large cell numbers by scalable expansion is essential for generating the large cell numbers required in clinical applications. In addition, the microcarrier system may allow efficient non-invasive harvesting. Efficient non-invasive harvesting is important for obtaining large quantities of non-compromised high-quality cells, and also this is a requirement for clinical applications. This may be achieved by (i) generating entirely thermoresponsive microsphere that contained a thermally responsive monomer crosslinked with a functional group monomer throughout the matrix, and displayed a significant volume and surface area change when the temperature was reduced. Additionally, the microsphere may have a polymer coating thereon.

The polymer coated microspheres may be used to prepare a wide variety of synthetic substrates that are compatible for a wide range of different cell types, including various types of human stem cells.

For example, about 90% of the cells may be easily harvested by thermal detachment from the microcarrier system, while hMSC morphology, immunophenotype and multipotency are being maintained after long-term scalable expansion (21 days) under xeno-free and fully defined conditions. The scalable thermoresponsive microcarrier systems may greatly facilitate hMSC applications in the future.

The invention claimed is:

1. A polymeric microsphere comprising a thermally responsive monomer crosslinked with a functional group monomer, wherein the functional group monomer comprises a primary amine functional group, wherein the microsphere further comprises a polymer coating selected from the group consisting of polymerized catecholamines, dopamine, L-3,4-dihydroxyphenylalanine, epinephrine, and norepinephrine, wherein the entire microsphere is coated with the polymer coating, and wherein the microsphere has a particle size in a range of 100 μm to 200 μm.

2. The polymeric microsphere of claim 1, wherein the thermally responsive monomer is selected from the group consisting of N-isopropylacrylamide, N,N-diethylacrylamide, 2-(dimethylamino)ethyl methacrylate, N,N-dimethylacrylamide, acrylamide, 2-(diethylamino)ethyl acrylate, 2-(acryloyloxyethyl) trimethylammonium chloride, vinylcaprolactam, methyl vinyl ether, hydroxyethylmethacrylate, 4-hydroxybutyl acrylate, 2-hydroxyethyl methacrylate, 3-hydroxypropyl methacrylate, 2-carboxyethyl acrylate, 2-carboxyethyl acrylate oligomers, and poly(ethylene glycol) methacrylate.

3. The polymeric microsphere of claim 1, wherein the primary amine functional group monomer is selected from the group consisting of 2-aminoethyl methacrylate hydrochloride, 3-aminopropyl methacrylate hydrochloride, and N-(3-aminopropyl) methacrylamide hydrochloride.

4. The polymeric microsphere of claim 1, wherein the thermally responsive monomer is crosslinked with the functional group monomer by a crosslinker comprising N,N'-methylenebis(acrylamide).

5. The polymeric microsphere of claim 1, wherein the particle size is in a range of 125 μm to 177 μm.

6. The polymeric microsphere of claim 1, wherein the polymeric microsphere is thermally responsive, such that upon a reduction in temperature from 37° C. to room temperature, the particle size of the polymeric microsphere increases in a range of more than 1-fold to 300-fold of the particle size of the polymeric microsphere prior to the reduction in temperature.

7. The polymeric microsphere of claim 1, wherein the polymeric microsphere is thermally responsive, such that upon reduction in temperature from 37° C. to room temperature, a hydrophilicity of a surface of the polymeric microsphere increases relative to the hydrophilicity of the surface prior to the reduction in temperature.

8. A method of preparing a polymeric microsphere comprising a thermally responsive monomer crosslinked with a functional group monomer, wherein the functional group monomer comprises a primary amine functional group, wherein the method comprises the steps of:
  i. providing a microemulsion mixture of the thermally responsive monomer, the functional group monomer and the cross-linker stirring at a temperature for a period of time;
  ii. polymerizing said microemulsion mixture with an initiator stirring at the temperature for a period of time to thereby synthesize said polymeric microsphere; and,
  iii. coating the entire polymeric microsphere with a polymer coating selected from the group consisting of polymerized catecholamines, dopamine, L-3,4-dihydroxyphenylalanine, epinephrine, and norepinephrine, wherein the microsphere has a particle size in a range of 100 μm to 200 μm.

9. The method of claim 8, wherein the temperature is room temperature, and the initiator is ammonium persulfate and/or N,N,N',N'-tetramethylethylenediamine.

10. The method of claim 8, wherein the temperature is in a range of 50° C. to 70° C., and the initiator is 2,2'-azobis[2-(2-imidazolin-2-yl)propane]dihydrochloride.

11. A method of culturing stem cells or stromal cells comprising the step of cultivating the stem cells or stromal cells on a surface coated on a polymeric microsphere, wherein said polymeric microsphere comprises a thermally responsive monomer crosslinked with a functional group monomer, and wherein the functional group monomer comprises a primary amine functional group, wherein the microsphere further comprises a polymer coating selected from the group consisting of polymerized catecholamines, dopamine, L-3,4-dihydroxyphenylalanine, epinephrine, and norepinephrine, wherein the entire microsphere is coated with the polymer coating, and wherein the microsphere has a particle size in a range of 100 μm to 200 μm.

12. The method of claim 11, wherein the method is undertaken in a serum-free condition.

13. The method of claim 11, wherein the method is undertaken in a xeno-free condition.

* * * * *

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Forward primer

<400> SEQUENCE: 1
acttccgctg gtcagatgga                                               20

<210> SEQ ID NO 2
<211> LENGTH: 20
<212> TYPE: DNA
<213> ORGANISM: Artificial Sequence
<220> FEATURE:
<223> OTHER INFORMATION: Reverse primer

<400> SEQUENCE: 2
tctcgtgcca gatcatcacc                                               20

<210> SEQ ID NO 3
<211> LENGTH: 28
<212> TYPE: DNA
<213> ORGANISM: Artificial Sequence
<220> FEATURE:
<223> OTHER INFORMATION: Forward primer

<400> SEQUENCE: 3
cggcaactct agtatttagg ataacctt                                      28

<210> SEQ ID NO 4
<211> LENGTH: 21
<212> TYPE: DNA
<213> ORGANISM: Artificial Sequence
<220> FEATURE:
<223> OTHER INFORMATION: Reverse primer

<400> SEQUENCE: 4
cacgatttgc tcccctact c                                              21

<210> SEQ ID NO 5
<211> LENGTH: 20
<212> TYPE: DNA
<213> ORGANISM: Artificial Sequence
<220> FEATURE:
<223> OTHER INFORMATION: Forward primer

<400> SEQUENCE: 5
caaggcacca tctccaggaa                                               20

<210> SEQ ID NO 6
<211> LENGTH: 24
<212> TYPE: DNA
<213> ORGANISM: Artificial Sequence
<220> FEATURE:
<223> OTHER INFORMATION: Reverse primer

<400> SEQUENCE: 6
aaagggtatt tgtggcagca tatt                                          24

<210> SEQ ID NO 7
<211> LENGTH: 19
<212> TYPE: DNA
<213> ORGANISM: Artificial Sequence

```
<220> FEATURE:
<223> OTHER INFORMATION: Forward primer

<400> SEQUENCE: 7
cagccgcttc acctacagc                                                19

<210> SEQ ID NO 8
<211> LENGTH: 25
<212> TYPE: DNA
<213> ORGANISM: Artificial Sequence
<220> FEATURE:
<223> OTHER INFORMATION: Reverse primer

<400> SEQUENCE: 8
ttttgtattc aatcactgtc ttgcc                                         25

<210> SEQ ID NO 9
<211> LENGTH: 20
<212> TYPE: DNA
<213> ORGANISM: Artificial Sequence
<220> FEATURE:
<223> OTHER INFORMATION: Forward primer

<400> SEQUENCE: 9
ggagatcgtg cagacaatga                                               20

<210> SEQ ID NO 10
<211> LENGTH: 20
<212> TYPE: DNA
<213> ORGANISM: Artificial Sequence
<220> FEATURE:
<223> OTHER INFORMATION: Reverse primer

<400> SEQUENCE: 10
gagctgtcct ggtagccaaa                                               20

<210> SEQ ID NO 11
<211> LENGTH: 20
<212> TYPE: DNA
<213> ORGANISM: Artificial Sequence
<220> FEATURE:
<223> OTHER INFORMATION: Forward primer

<400> SEQUENCE: 11
tggtggaatg cgtcatgaaa                                               20

<210> SEQ ID NO 12
<211> LENGTH: 20
<212> TYPE: DNA
<213> ORGANISM: Artificial Sequence
<220> FEATURE:
<223> OTHER INFORMATION: Reverse primer

<400> SEQUENCE: 12
caacgtccct tggcttatgc                                               20

<210> SEQ ID NO 13
<211> LENGTH: 18
<212> TYPE: DNA
<213> ORGANISM: Artificial Sequence
<220> FEATURE:
<223> OTHER INFORMATION: Forward primer

<400> SEQUENCE: 13
gaaggtgaag gtcggagt                                                 18
```

```
<210> SEQ ID NO 14
<211> LENGTH: 20
<212> TYPE: DNA
<213> ORGANISM: Artificial Sequence
<220> FEATURE:
<223> OTHER INFORMATION: Reverse primer

<400> SEQUENCE: 14
gaagatggtg atgggatttc                                              20

<210> SEQ ID NO 15
<211> LENGTH: 19
<212> TYPE: DNA
<213> ORGANISM: Artificial Sequence
<220> FEATURE:
<223> OTHER INFORMATION: Forward primer

<400> SEQUENCE: 15
gccagttgca gccttctca                                               19

<210> SEQ ID NO 16
<211> LENGTH: 24
<212> TYPE: DNA
<213> ORGANISM: Artificial Sequence
<220> FEATURE:
<223> OTHER INFORMATION: Reverse primer

<400> SEQUENCE: 16
aaagcaaatc actgcaattc tcat                                         24

<210> SEQ ID NO 17
<211> LENGTH: 21
<212> TYPE: DNA
<213> ORGANISM: Artificial Sequence
<220> FEATURE:
<223> OTHER INFORMATION: Forward primer

<400> SEQUENCE: 17
tccctgcttg aggaggaagt t                                            21

<210> SEQ ID NO 18
<211> LENGTH: 17
<212> TYPE: DNA
<213> ORGANISM: Artificial Sequence
<220> FEATURE:
<223> OTHER INFORMATION: Reverse primer

<400> SEQUENCE: 18
cacgctgccg tcagcat                                                 17

<210> SEQ ID NO 19
<211> LENGTH: 20
<212> TYPE: DNA
<213> ORGANISM: Artificial Sequence
<220> FEATURE:
<223> OTHER INFORMATION: Forward primer

<400> SEQUENCE: 19
gagggcgatc ttgacaggaa                                              20

<210> SEQ ID NO 20
<211> LENGTH: 24
<212> TYPE: DNA
<213> ORGANISM: Artificial Sequence
<220> FEATURE:
<223> OTHER INFORMATION: Reverse primer
```

```
<400> SEQUENCE: 20
tctcccatca ttaaggaatt catg                                              24

<210> SEQ ID NO 21
<211> LENGTH: 19
<212> TYPE: DNA
<213> ORGANISM: Artificial Sequence
<220> FEATURE:
<223> OTHER INFORMATION: Forward primer

<400> SEQUENCE: 21
cgtggccttc aaggtggta                                                    19

<210> SEQ ID NO 22
<211> LENGTH: 23
<212> TYPE: DNA
<213> ORGANISM: Artificial Sequence
<220> FEATURE:
<223> OTHER INFORMATION: Reverse primer

<400> SEQUENCE: 22
cggagctcag cagaataatt ttc                                               23

<210> SEQ ID NO 23
<211> LENGTH: 19
<212> TYPE: DNA
<213> ORGANISM: Artificial Sequence
<220> FEATURE:
<223> OTHER INFORMATION: Forward primer

<400> SEQUENCE: 23
agtacccgca cttgcacaa                                                    19

<210> SEQ ID NO 24
<211> LENGTH: 24
<212> TYPE: DNA
<213> ORGANISM: Artificial Sequence
<220> FEATURE:
<223> OTHER INFORMATION: Reverse primer

<400> SEQUENCE: 24
ctcgttcaga agtctccaga gctt                                              24
```